(12) United States Patent
Li et al.

(10) Patent No.: US 8,877,254 B2
(45) Date of Patent: *Nov. 4, 2014

(54) IN SITU GENERATION OF PEROXYCARBOXYLIC ACIDS AT ALKALINE PH, AND METHODS OF USE THEREOF

(75) Inventors: Junzhong Li, Apple Valley, MN (US); David D. McSherry, St. Paul, MN (US); Richard Staub, Lakeville, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/331,486

(22) Filed: Dec. 20, 2011

(65) Prior Publication Data

US 2012/0172441 A1 Jul. 5, 2012

Related U.S. Application Data

(60) Provisional application No. 61/427,965, filed on Dec. 29, 2010.

(51) Int. Cl.

| A61L 2/18 | (2006.01) |
|---|---|
| C07C 409/24 | (2006.01) |
| C07C 69/30 | (2006.01) |
| C07C 309/04 | (2006.01) |
| C07C 309/20 | (2006.01) |
| C07C 309/22 | (2006.01) |
| A01N 37/16 | (2006.01) |
| A01N 37/12 | (2006.01) |

(52) U.S. Cl.
CPC .............. *C07C 409/24* (2013.01); *A01N 37/16* (2013.01); *A01N 37/12* (2013.01)
USPC ............ 424/616; 562/2; 562/3; 562/4; 562/6; 422/28; 568/568

(58) Field of Classification Search
CPC ......... A61L 2/18; A61L 2/186; C07C 409/24; C07C 309/04; C07C 309/20; C07C 309/22; C07C 69/30; D06L 3/25
USPC ..................... 562/6, 2, 3, 4; 422/28; 424/616; 568/568

See application file for complete search history.

(56) References Cited

U.S. PATENT DOCUMENTS

| 2,955,905 | A | 10/1960 | Davies et al. |
|---|---|---|---|
| 2,995,524 | A * | 8/1961 | Wylie et al. .................... 510/536 |
| 3,256,198 | A | 6/1966 | Matzner |
| 3,272,750 | A | 9/1966 | Chase |
| 3,432,546 | A | 3/1969 | Oringer et al. |
| 3,847,830 | A | 11/1974 | Williams et al. |
| 3,925,234 | A | 12/1975 | Hachmann et al. |
| 4,003,841 | A | 1/1977 | Hachmann et al. |
| 4,051,058 | A | 9/1977 | Böwing et al. |
| 4,126,573 | A | 11/1978 | Johnston |
| 4,170,453 | A | 10/1979 | Kitko |
| 4,233,235 | A | 11/1980 | Camden et al. |
| 4,370,251 | A | 1/1983 | Liao et al. |
| 4,412,934 | A | 11/1983 | Chung et al. |
| 4,483,778 | A | 11/1984 | Thompson et al. |
| 4,486,327 | A | 12/1984 | Murphy et al. |
| 4,617,090 | A | 10/1986 | Chum et al. |
| 4,655,781 | A | 4/1987 | Hsieh et al. |
| 4,778,618 | A | 10/1988 | Fong et al. |
| 4,964,870 | A | 10/1990 | Fong et al. |
| 5,030,240 | A | 7/1991 | Wiersema et al. |
| 5,143,641 | A | 9/1992 | Nunn |
| 5,200,189 | A | 4/1993 | Oakes et al. |
| 5,314,687 | A | 5/1994 | Oakes et al. |
| 5,431,849 | A | 7/1995 | Damhus et al. |
| 5,503,765 | A | 4/1996 | Schepers et al. |
| 5,505,740 | A | 4/1996 | Kong et al. |
| 5,637,755 | A | 6/1997 | Nagumo et al. |
| 5,681,805 | A | 10/1997 | Scheuing et al. |
| 5,716,923 | A | 2/1998 | MacBeath |
| 5,718,910 | A | 2/1998 | Oakes et al. |
| 5,827,447 | A | 10/1998 | Tamura et al. |
| 5,827,808 | A | 10/1998 | Appleby et al. |
| 5,977,403 | A | 11/1999 | Byers |
| 5,998,350 | A | 12/1999 | Burns et al. |
| 6,022,381 | A | 2/2000 | Dias et al. |
| 6,177,393 | B1 | 1/2001 | McGregor et al. |
| 6,207,632 | B1 | 3/2001 | Brooker et al. |

(Continued)

FOREIGN PATENT DOCUMENTS

| EP | 0267047 A2 | 5/1988 |
|---|---|---|
| JP | 62155203 A | 7/1987 |

(Continued)

OTHER PUBLICATIONS

Ecolab USA, Inc. et al., PCT/IB2011/055830 filed Dec. 20, 2011, "Notification of Transmittal of The International Search Report and The Written Opinion of the International Searching Authority, or the Declaration" mailed Aug. 24, 2012, 8 pages.

Ecolab USA, Inc. et al., PCT/IB2011/055832 filed Dec. 20, 2011, "Notification of Transmittal of The International Search Report and The Written Opinion of the International Searching Authority, or the Declaration" mailed Aug. 14, 2012, 14 pages.

Dannacher, Josef J., "Catalytic bleach: Most valuable applications for smart oxidation chemistry", Journal of Molecular Catalysis A: Chemical 251 (2006) 159-176.

Rusch gen. Klaas, Mark et al., "Biocatalytic peroxy acid formation for disinfection", Journal of Molecular Catalysis B: Enzymatic 19-20 (2002) 499-505.

Rusch gen. Klaas, Mark et al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.

(Continued)

*Primary Examiner* — Sreeni Padmanabhan
*Assistant Examiner* — Irina Neagu
(74) *Attorney, Agent, or Firm* — McKee, Voorhees & Sease

(57) ABSTRACT

The present disclosure is related to percarboxylic acid compositions formed in situ in non-equilibrium reactions. The peroxycarboxylic acid compositions are formed using ester based starting materials. Methods for using the percarboxylic acid compositions are also disclosed.

22 Claims, 6 Drawing Sheets

(56) References Cited

U.S. PATENT DOCUMENTS

| | | |
|---|---|---|
| 6,221,341 B1 | 4/2001 | Montgomery |
| 6,399,564 B1 | 6/2002 | Speed et al. |
| 6,569,286 B1 | 5/2003 | Withenshaw et al. |
| 6,599,871 B2 | 7/2003 | Smith |
| 6,602,845 B2 | 8/2003 | Connor et al. |
| 6,649,140 B2 | 11/2003 | Paparatto et al. |
| 6,689,732 B1 | 2/2004 | Guedira et al. |
| 7,012,154 B2 | 3/2006 | Vineyard et al. |
| 7,189,385 B2 | 3/2007 | Montgomery |
| 7,217,295 B2 | 5/2007 | Samain et al. |
| 7,569,232 B2 | 8/2009 | Man et al. |
| 7,598,218 B2 | 10/2009 | Stolte et al. |
| 7,915,445 B2 | 3/2011 | Maatta et al. |
| 7,919,122 B2 | 4/2011 | Okano et al. |
| 2003/0100469 A1 | 5/2003 | Connor et al. |
| 2004/0097410 A1* | 5/2004 | Zheng et al. .................. 514/3 |
| 2005/0008526 A1 | 1/2005 | Bianchetti et al. |
| 2005/0109981 A1 | 5/2005 | Tucker et al. |
| 2006/0173209 A1 | 8/2006 | Vineyard et al. |
| 2007/0274857 A1 | 11/2007 | Okano et al. |
| 2008/0176784 A1 | 7/2008 | Clowes et al. |
| 2009/0018049 A1 | 1/2009 | Stolte et al. |
| 2010/0084603 A1 | 4/2010 | Narayan et al. |
| 2010/0286017 A1* | 11/2010 | Righetto .................. 510/283 |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |

FOREIGN PATENT DOCUMENTS

| | | |
|---|---|---|
| JP | 5186989 | 7/1993 |
| JP | 6305920 | 11/1994 |
| WO | 9115474 A1 | 10/1991 |
| WO | 9403395 A1 | 2/1994 |
| WO | 9424869 A1 | 11/1994 |
| WO | 9614384 A1 | 5/1996 |
| WO | 9616148 A1 | 5/1996 |
| WO | 9803513 A1 | 1/1998 |
| WO | 9931215 A1 | 6/1999 |
| WO | 2010050634 A1 | 5/2010 |

OTHER PUBLICATIONS

Tsunokawa, Youko et al., "A Versatile Method for Preparation of O-Alkylperoxycarbonic Acids: Epoxidation with Alkyloxcarbonylimidazoles and Hydrogen Peroxide", Tetrahedron Letters, vol. 23, No. 20, (1982), pp. 2113-2116.

Yin, De Lu (Tyler), et al., "Switching Catalysis from Hydrolysis to Perhydrolysis in *Pseudomonas fluorescens* Esterase", Biochemistry, (2010), 49, 1931-1942.

English Abstract of JP62155203, published on Jul. 10, 1987 (1 page).

English Abstract of JP6305920, published on Nov. 1, 1994 (1 page).

Caboni-Oerlemans, Chiara, et al., "Hydrolase-catalysed synthesis of peroxycarboxylic acids: Biocatalytic promiscuity for practical applications", ELSEVIER, Journal of Biotechnology, 126 (2006) 140-151 (12 pages).

Effkemann, Stefan, et al., "Peroxide analysis in laundry detergents using liquid chromatography", ELSEVIER, Analytica Chimica Acta, 363 (1998) 97-103 (7 pages).

Leveneur, Sebastien, "Synthesis of peroxypropionic acid from propionic acid and hydrogen peroxide over heterogeneous catalysts", ELSEVIER, Chemical Engineering Journal, 147 (2009) 323-329 (7 pages).

Maeda, Hatsuo, et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", Pharmaceutical Society of Japan, Cehm. Pharm. Bull. 50(2) 169-174, 2002 (6 pages).

Muurinene, Esa, "Organosolv Pulping—A review and distillation study related to peroxyacid pulping", Department of Process Engineering, University of Oulu, May 16, 2000, Oulu, Finland (314 pages).

Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).

Rusch gen. Klaas, Mark, et al., "Lipase-catalyzed preparation of peroxy acids and their use for expoxidation", ELSEVIER, Journal of Molecular Catalysis A: Chemical 117 (1997) 311-319 (9 pages).

\* cited by examiner

IN SITU GENERATION OF PEROXYCARBOXYLIC ACIDS AT ALKALINE PH, AND METHODS OF USE THEREOF

CROSS REFERENCE TO RELATED APPLICATIONS

This application is a nonprovisional application of U.S. Provisional Application No. 61/427,965, filed Dec. 29, 2010, entitled In Situ Generation of Peroxycarboxylic Acids at Alkaline pH and Methods of Use Thereof, which is herein incorporated by reference in its entirety.

This application is related to U.S. patent application Ser. No. 13/331,304, entitled In Situ Generation of Peroxycarboxylic Acids at Alkaline pH and Methods of Use Thereof, U.S. patent application Ser. Nos. 61/427,951 and 13/330,915, entitled Sugar Ester Peracid On-Site Generator and Formulator, U.S. patent application Ser. No. 13/330,981, entitled Continuous On-Line Adjustable Disinfectant/Sanitizer/Bleach Generator, U.S. patent application Ser. No. 13/331,104, entitled Generation of Peroxycarboxylic Acids at Alkaline pH, and Their Use as Textile Bleaching and Antimicrobial Agents, and U.S. patent application Ser. No. 13/331,385, entitled Water Temperature as a Means of Controlling Kinetics of Onsite Generated Peracids, each filed concurrently herewith. The entire contents of these patent applications are hereby expressly incorporated herein by reference including, without limitation, the specification, claims and abstract, as well as any figures, tables or drawings thereof.

FIELD OF THE INVENTION

The present disclosure relates to compositions and methods for the in situ generation of peroxycarboxylic acid compositions, at alkaline pH levels, viz. greater than about pH 12. The present disclosure also relates to methods for the in situ generation of mixed percarboxylic acid compositions, and methods of using the in situ generated peroxycarboxylic acid compositions.

BACKGROUND OF THE INVENTION

Peroxycarboxylic acids are known for use as antimicrobials and bleaching agents. Mixed peroxycarboxylic acid systems are also known for use as antimicrobial and bleaching agents. However, there are disadvantages to use of these antimicrobial and bleaching agents. For example, the most commonly used peroxycarboxylic acid, peroxyacetic acid, is known to have a strong pungent odor. In addition, peracids such as peroxycarboxylic acid have known chemical disadvantages, namely, they are relatively unstable in solution and decompose to the corresponding carboxylic acids and oxygen.

Conventional peroxycarboxylic acid compositions are made through an acid catalyzed equilibrium reaction. Most often, the peroxycarboxylic acids are generated in a chemical plant, and then shipped to customers for on-site use. Due to the limited storage stability of peroxycarboxylic acids, the peroxycarboxylic acids must be packed in special containers and shipped under the strict Department of Transportation (DOT) guidelines. Certain improvements to peroxycarboxylic acid stability have proved advantageous for shipping purposes, as described in U.S. patent application Ser. No. 11/847,604, entitled "Shelf Stable, Reduced Corrosion, Ready to Use Peroxycarboxylic Acid Antimicrobial Compositions," the entire contents of which are hereby expressly incorporated herein by reference. Most commercially available products in an equilibrium mixture contain excess hydrogen peroxide in the presence of stabilizers and acid catalysts, to stabilize and improve the composition's shelf life. Despite such stability improvements, excess amounts of reagents (e.g., acids, oxidizing agents, and stabilizers) are present in the compositions during shipping to prevent decomposition. These and other disadvantages to the use of peracid compositions exist.

Accordingly, it is an objective of the claimed invention to develop in situ methods for generation of peroxycarboxylic acids at alkaline pH.

A further object of the invention is an in situ method for generation of stable single peracid systems that are substantially free of stabilizing agents and/or surfactants.

A further object of the invention is an in situ method for generation of stable mixed peracid systems that are substantially free of stabilizing agents and/or surfactants.

A still further object of the invention is to develop concentrated peracid chemistries for further dilution and/or use on site within a matter of hours to days in order to eliminate the need for various stabilizing agents in the compositions to ensure storage stability (e.g. stability for at least one year as required for regulated chemistries).

BRIEF SUMMARY OF THE INVENTION

In some aspects, the present disclosure relates to peroxycarboxylic acid forming compositions. The compositions comprise a first reagent premix comprising at least one ester of a polyhydric alcohol and a C1 to C18 carboxylic acid, and one or more agents selected from the group consisting of an oxidizing agent, a dispersing agent, a solvent, water and mixtures thereof; wherein the solvent is an organic solvent to solubilize the ester; wherein the dispersing agent is sufficient to create a physically meta-stable solution upon reaction with a source of alkalinity and the subsequent acidification; and a second reagent source comprising the source of alkalinity; wherein said composition is not at equilibrium, has a pH greater than about 12, and is substantially free of a stabilizing agent.

In other aspects, the present disclosure relates a peroxycarboxylic acid forming composition comprising a first reagent premix comprising at least one ester of a polyhydric alcohol and a C1 to C18 carboxylic acid, an oxidizing agent and a dispersing agent; wherein the dispersing agent is sufficient to create a physically meta-stable solution upon reaction with a source of alkalinity and the subsequent acidification; and a second reagent source comprising a source of alkalinity; wherein said composition is not at equilibrium, has a pH greater than about 12, and is substantially free of a stabilizing agent.

In other aspects, the present disclosure relates to methods for delivering an antimicrobial comprising contacting the surface with an antimicrobial composition formed by diluting a composition first reagent premix comprising at least one ester of a polyhydric alcohol and a C1 to C18 carboxylic acid, an oxidizing agent and a dispersing agent, and a second reagent source comprising a source of alkalinity, with an aqueous acidic solution to a pH of about 1 to about 8, wherein the solvent is an organic solvent to solubilize the ester; and wherein the dispersing agent is sufficient to create a physically meta-stable solution upon reaction with a source of alkalinity.

In other aspects, the present disclosure provides a method for forming an antimicrobial composition, comprising: (a) providing a peroxycarboxylic acid composition having active peroxycarboxylic acid content from about 0.25% to about 20% comprising: (i) a first reagent premix comprising at least one ester of a polyhydric alcohol and a C1 to C18 carboxylic acid, and one or more agents selected from the group consisting of an oxidizing agent, a dispersing agent, a solvent, water and mixtures thereof; wherein the solvent is an organic solvent to solubilize the ester; wherein the dispersing agent is sufficient to create a physically meta-stable solution upon reaction with a source of alkalinity; and (ii) a second reagent source comprising a source of alkalinity; wherein said composition has a pH greater than 12 and is not at equilibrium; (b) diluting the peroxycarboxylic acid composition to an alkaline solution having an active peroxycarboxylic acid content from about 0.01% to about 1%; (c) providing an acidic aqueous solution; and (d) diluting the peroxycarboxylic acid composition with the acidic aqueous solution to a pH of about 1.0 to about 8.0 to form the antimicrobial composition.

In still yet other aspects, the present disclosure provides methods for forming an antimicrobial composition comprising: (a) providing a peroxycarboxylic acid composition having active peroxycarboxylic acid content from about 0.25% to about 20% comprising: (i) a first reagent premix comprising at least one ester of a polyhydric alcohol and a C1 to C18 carboxylic acid, and one or more agents selected from the group consisting of an oxidizing agent, a dispersing agent, a solvent, water and mixtures thereof; wherein the dispersing agent is sufficient to create a physically meta-stable solution upon reaction with a source of alkalinity; and (ii) a second reagent source comprising a source of alkalinity; wherein said composition has a pH greater than 12 and is not at equilibrium; (b) allowing the peroxycarboxylic acid composition to react for a sufficient amount of time such that a C1 to C18 percarboxylic acid is formed to generate an antimicrobial composition; and (c) providing said composition to an application for use without an acidification step.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
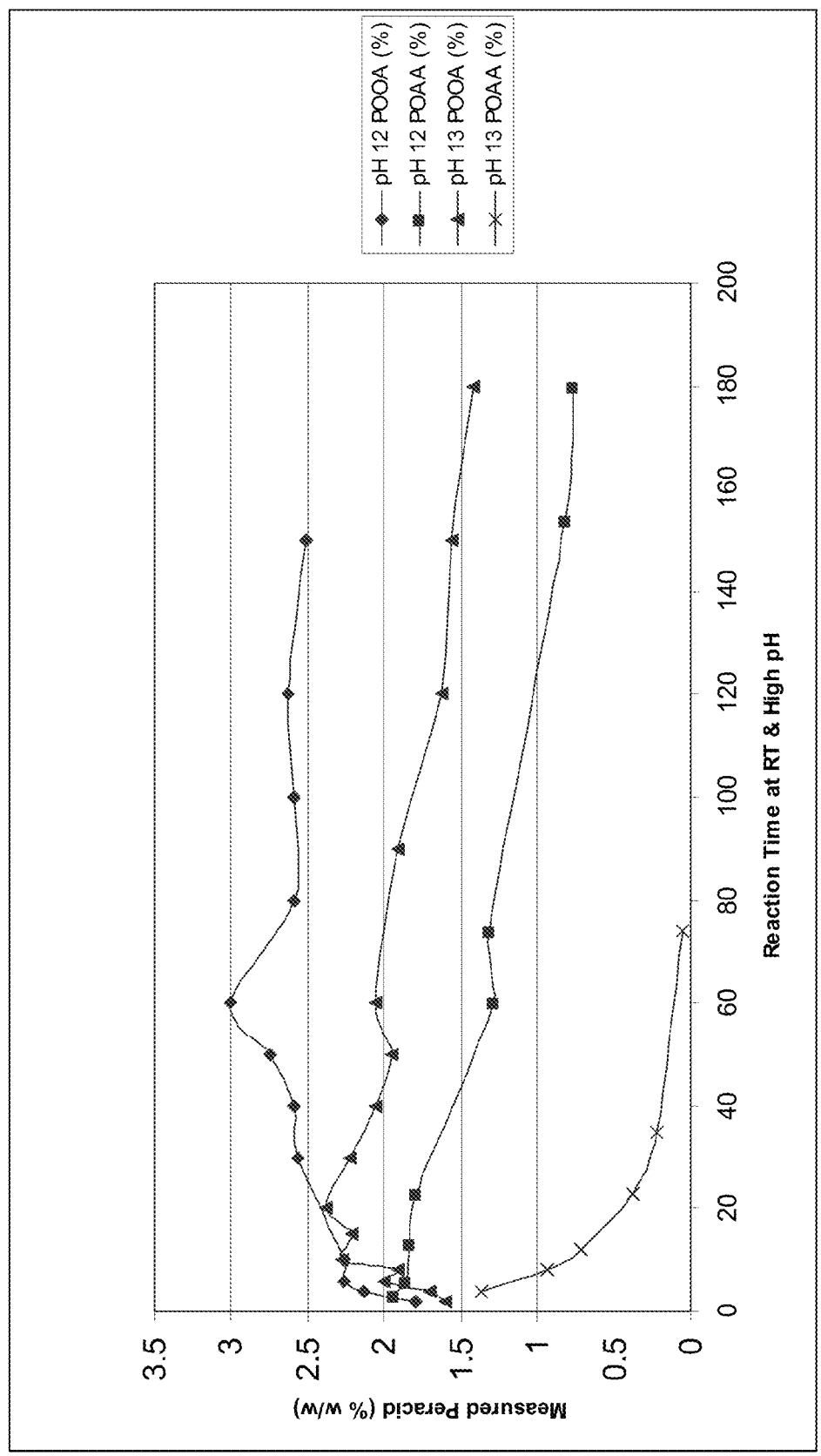
FIG. 1 is a graphical depiction of the stability of various peroxycarboxylic acid compositions formed from esters at an alkaline pH over time.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to peroxycarboxylic acid compositions generated in situ from a non-equilibrium ester based reaction, as well as methods of making and using such compositions. The compositions disclosed herein have many advantages over conventional, equilibrium based peroxycarboxylic acid compositions. For example, after peroxycarboxylic acid formation according to methods disclosed herein, the compositions have significantly lower levels of reactant residues compared to peroxycarboxylic acid compositions generated using equilibrium reactions. Further, as the compositions are generated in situ, and can be generated on site, the compositions can be substantially free of, or even free of, stabilizers. Additionally, due to the ability to generate the disclosed peroxycarboxylic acid compositions on site, the step of shipping hazardous peroxycarboxylic acid compositions to an end user can be eliminated. This beneficially allows a user to provide diluted compositions for a particular application without having to ship large amounts of a diluted composition. These and other benefits of the present invention are disclosed herein.

The embodiments of this invention are not limited to particular peroxycarboxylic acid compositions and methods for in situ generation of the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the phrase "air streams" includes food anti-spoilage air circulation systems. Air streams also include air streams typically encountered in hospital, surgical, infirmity, birthing, mortuary, and clinical diagnosis rooms.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "cleaning," as used herein, means to perform or aid in soil removal, bleaching, microbial population reduction, or combination thereof.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "fouling" shall be understood to mean the undesirable presence of or any deposition of any organic or inorganic material in the applicable composition or chemistry.

As used herein, the term "free" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthroscopes) and related equipment, and the like, or combinations thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid (POAA) and peroxyoctanoic acid (POOA).

As used herein, the terms "mixed," "mixture" or "more than one" when used relating to esters suitable for use in forming the compositions of the invention refer to a composition or mixture including more than one ester group undergoing a perhydrolysis reaction to form the peroxycarboxylic composition. The use of at least one ester of a polyhydric alcohol and a C1 to C18 carboxylic acid according to the invention includes the use of various forms of the ester, such as the mono, di, tri and/or mixtures thereof formations of the particular ester. Accordingly, examples of suitable forms of esters for use as "mixtures" or comprising "more than one" include, but are not limited to, glycerol monooctanoate, glycerol dioctanoate, glycerol trioctanoate, sorbitan monooctanoate, sorbitan dioctanoate, sorbitan trioctanoate, and mixtures and derivatives thereof. Further, as one skilled in the art shall ascertain based upon the description of the invention disclosed herein, the use of an ester source, such as glycerol octanoate, may further comprise the use of the mono, di and tri esters and/or mixtures thereof. According to various embodiments of the invention, the use of "an" ester, such as octanoic glyceride, may include the use of a "mixture" of esters wherein more than one formation of the ester is present, including for example the mono, di and tri formations and/or mixtures thereof.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof.

As used herein, the terms "peracid" or "peroxy acid" refer to an acid having the hydrogen of the hydroxyl group replaced by a hydroxy group. Oxidizing peracids are referred to herein as peroxycarboxylic acids.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the term "polyhydric alcohol" or "polyol," refers to an alcohol that has two or more hydroxyl groups. Polyhydric alcohols suitable for use in the compositions include, but are not limited to, sugars, sugar alcohols, and mixtures and derivatives thereof.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein the term "sugar" refers to carbohydrates including one, two, or more saccharose groups. Sugars are a group of organic compounds related by molecular structure that comprise simpler members of the general class of carbohydrates. Each sugar consists of a chain of 2 to 7 carbon atoms (usually 5 or 6). Sugars have the general formula $C_2H_{2n}O_n$, wherein n is between 2 and 7. One of the carbons carries aldehydic or ketonic oxygen which may be combined in acetal or ketal forms and the remaining carbon atoms usually bear hydrogen atoms and hydroxyl groups. In general, sugars are more or less sweet, water soluble, colorless, odorless, optically active substances which lose water, caramelize and char when heated. Exemplary sugars include, but are not limited to, glucose, sucrose, lactose and mixtures thereof.

As used herein, the term "sugar alcohol" refers to the hydrogenated form of a carbohydrate, wherein the carbonyl group of the carbohydrate has been reduced to a primary or secondary hydroxyl group. Sugar alcohols have the general formula $CH_2OH(CHOH)_nCH_2OH$, wherein n is from 2 to 5. Exemplary sugar alcohols include, but are not limited to, glycol, ethylene glycol, propylene glycol, glycerol, erythritol, pentaerythritol, threitol, arabitol, xylitol, ribitol, mannitol, sorbitol, sorbitan, dulcitol, iditol, inositol, isomalt, maltitol, lactitol, polyglycitol, 1,4-cyclohexane diol, and mixtures and derivatives thereof. In some embodiments, the sugar alcohol is selected from ethylene glycol, propylene glycol, glycerol, polyglycerol, sorbitol, sorbitan, and mixtures and derivatives thereof.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "ware washing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

EMBODIMENTS OF THE INVENTION

In some aspects, the present disclosure relates to a non-equilibrium or stoichiometric peroxycarboxylic acid forming compositions, and methods of making and using the compositions. Peroxycarboxylic acids are known for use as antimicrobials and bleaching agents. Conventional peroxycarboxylic acid compositions are formed through an acid catalyzed equilibrium reaction. Although acid catalyzed equilibrium reactions are commonly used to generate peroxycarboxylic acids, there are many downsides to such compositions, including, but not limited to the use of excess amounts of reactants required to drive the equilibrium reaction, along with the hazardous shipping conditions required to provide a customer the peroxycarboxylic acid compositions. The present compositions, and methods of forming them, according to the invention avoid these issues.

While an understanding of the mechanism is not necessary to practice the present invention and while the present invention is not limited to any particular mechanism of action, it is contemplated that, in some embodiments the benefits afforded according to the invention result from the production of a non-equilibrium chemistry. Beneficially, the reacted peracids according to the invention are obtained in greater amounts than in equilibrium chemistry wherein greater amounts of unreacted hydrogen peroxide and other reagents would be present. According to the present invention, an aqueous solution of the peroxycarboxylic acid(s) produced contains a relatively higher concentration of peroxycarboxylic acid(s) compared to unreacted hydrogen peroxide component. This is significantly advantageous for the antimicrobial, disinfectant, bleaching and other cleaning applications disclosed herein as desirable according to the embodiments of the invention.

In some aspects, the methods of the invention generate peracid from about 0.25% to about 20%. In some aspects, the methods of the invention generate peracid of about 2%, at least about 3%, preferably at least about 4%, more preferably at least about 5%, and still most preferably at least about 6% peracid from the reaction mixtures (reagents) according to the invention, namely the reaction of an ester or a mixture of esters of a polyhydric alcohol and a C1 to C18 carboxylic acid, a source of alkalinity, an oxidizing agent, and optionally an acidulating agent. Rather than providing a peracid composition in an equilibrium mixture, in situ generation of the peracid composition allows the peracids to be produced stoichiometrically through selecting the composition of the starting materials. The in situ systems according to the invention therefore generate higher concentrations of the peroxycarboxylic acid(s) than are available in equilibrium systems. In particular, according to the invention the systems generate higher concentrations of the peroxycarboxylic acid(s) and lower concentrations of hydrogen peroxide (e.g. unreacted reagents) than achieved in equilibrium systems. In addition, the methods of the present invention generate peroxycarboxylic acid(s) under alkaline conditions and thereafter adjust to acidic conditions to stabilize the peroxycarboxylic acid(s) and ensure the peroxycarboxylic acid(s) compositions do not disassociate, thereby providing stability for a sufficient amount of time to allow the use of the compositions on site after generation, preferably within a matter of hours or days.

As referred to herein, peroxycarboxylic acid forming compositions according to the invention refer to the generation of peroxycarboxylic acids in situ, in a non-equilibrium reaction. In particular embodiments of the invention, the methods produce the anion capable of forming peroxycarboxylic acid upon acidification. According to additional aspects of the invention, the methods may produce peroxycarboxylic acid compositions upon acidification.

Compositions

In some aspects, the present disclosure relates to peroxycarboxylic acid forming compositions. That is, the compositions are capable of generating peroxycarboxylic acids in situ, in a non-equilibrium reaction. Surprisingly, it has been found that the optimum pH for the generation of peroxycarboxylic acid compositions is greater than about 12, or pH greater than about 13. It has also been found that mixed peroxycarboxylic acid compositions, viz. compositions that form two or more peroxycarboxylic acids, can be generated in situ in accordance with the methods disclosed herein. Peroxycarboxylic (or percarboxylic) acids generally have the formula $R(CO_3H)n$, where, for example, R is an alkyl, aryl alkyl, cycloalkyl, aromatic, or heterocyclic group, and n is one, two, or three, and named by prefixing the parent acid with peroxy. The R group can be saturated or unsaturated as well as substituted or unsubstituted.

In an embodiment of the invention the peroxycarboxylic acid forming compositions comprise individual reagents combined according to the invention. These reagents are described herein individually along and include at least one ester of a polyhydric alcohol and a C1 to C18 carboxylic acid, an oxidizing agent, a source of alkalinity, solvents, and other functional groups. An acidulant is also described herein as a reagent to be added to the compositions after the formation of the percarboxylic acid(s). Alternatively, as described herein, there may be benefits to providing the reagents in various premix formulations to decrease the number of reagents and/or increase the simplicity of the invention. Each of these embodiments are described in further detail herein.

Esters

In some aspects, the compositions include an ester of a polyhydric alcohol and a C1 to C18 carboxylic acid. According to an embodiment, the polyhydric alcohol may also include a sugar alcohol. The compositions can also include more than one or a mixture of esters of a polyhydric alcohol and a C1 to C18 carboxylic acid. For example, in some embodiments, the compositions include two, three or four esters. When more than one ester is present, the esters can be different. For example, in some embodiments, the compositions can include a first ester of a polyhydric alcohol and a C1 to C4 carboxylic acid, and a second ester of a polyhydric alcohol and a C5 to C11 carboxylic acid. For further example, in some embodiments, the compositions can include a first ester of a polyhydric alcohol and a C1 to C18 carboxylic acid in a mono, di or tri-formation, and a second ester of a polyhydric alcohol and a C1 to C18 carboxylic acid in a mono, di or tri-formation. One skilled in the art will appreciate the various combinations of esters that can be used for the compositions according to the invention.

An example of a suitable ester for use according to the invention is glycerol octanoate. Glycerol octanoate has multiple ester components and others, including glycerol monooctanoate, glycerol dioctanoate, glycerol trioctanoate and others (glycerin, fatty acid, water). An estimated component percentage of each is approximated at about 39.6% glycerol monooctanoate, 24.5% glycerol dioctanoate, 1.42% glycerol trioctanoate and 34.5% of the others (glycerin, fatty acid, water).

The use of various forms of an ester (e.g. mono, di and/or tri-formations) to comprise a mixture of esters will impact the peracid yield of a particular composition according to the invention. For example, the various forms of the ester will have different kinetics in generating the peracids according to the methods of the invention. For example, in one aspect, a monooctanoate glycerol ester is faster in generating peracid than the di- or trioctanoate glycerol esters. In addition, the selection of the various forms of an ester will be further impacted by the water solubility of the compositions and whether any additional ingredients are combined to affect solubility (e.g. solvents) that would favor the use of less soluble ester forms (e.g. tri-formations). Accordingly, one skilled in the art of reaction kinetics will ascertain the benefits of using various combinations or mixtures of esters according to the compositions and methods of the invention.

The esters for use in the present invention include esters of polyhydric alcohols with carboxylic acid based leaving groups. A variety of carboxylic acids can be included. Carboxylic acids generally have the formula $R(COOH)n$, where, for example, R is an alkyl, aryl alkyl, cycloalkyl, aromatic, or heterocyclic group, and n is one, two, or three. In some embodiments, the carboxylic acid leaving group is a $C_5$ to $C_{11}$ carboxylic acid. In some embodiments, the carboxylic acid leaving group is a $C_1$ to $C_4$ carboxylic acid. In other embodiments, the compositions include two esters of polyhydric alcohols, each ester having a different carboxylic acid leaving group. For example, the compositions can include a polyhydric alcohol ester with a C1 to C4 carboxylic acid leaving group, and also include a polyhydric alcohol ester with a C5 to C11 carboxylic acid leaving group.

Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

Without wishing to be bound by any particular theory, it is thought that the esters included in the compositions undergo a perhydrolysis reaction, thereby forming the peroxycarboxylic composition. An exemplary perhydrolysis reaction in accordance with the present disclosure is illustrated below:

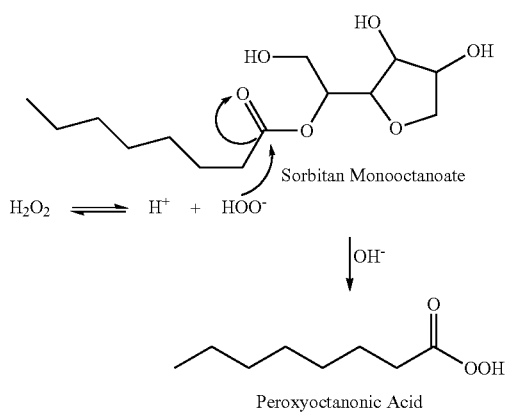

Sorbitan Monooctanoate $H_2O_2 \rightleftharpoons H^+ + HOO^-$ $\downarrow OH^-$ Peroxyoctanonic Acid As can be seen from this illustration, it is thought the oxidizing agent, $H_2O_2$, perhydrolyzes the ester bond, thereby forming the percarboxylic acid corresponding to the cleaved carboxylic acid group. In contrast to an acid catalyzed equilibrium reaction, the reaction is stoichiometric, i.e. no excess amounts of the reactants are required for the reaction. The kinetics of the reaction are pH dependent, and the reaction can reach the maximum yield in the order of minutes. Esters suitable for use include, but are not limited to, monooctanoic glyceride, dioctanoic glyceride, trioctaonoic glyceride, polyglycerol octanoate, sorbitan monooctanoate, sorbitan dioctanoate, sorbitan trioctanoate, laurate sucroside and mixtures and derivatives thereof.

The compositions include the esters in an amount sufficient to generate the desired amount of percarboxylic acid. In some embodiments, the compositions include about 0.01 wt-% to about 95 wt-% of the ester, about 0.1 wt-% to about 50 wt-% of the ester, or about 1 wt-% to about 10 wt-% of the ester. In some embodiments, more than one ester is present in the compositions. Each ester can be present in the compositions at the above stated weight percents.

Unlike conventional acid catalyzed equilibrium peroxycarboxylic acid forming compositions, the compositions of the present invention can be formed using a non-equilibrium perhydrolysis reaction. Thus, an excess amount of the starting reagents is not needed. Accordingly, after formation of the peroxycarboxylic acid, the compositions contain less carboxylic acid and more peroxycarboxylic acid than an equivalent equilibrium reaction. In some embodiments, the compositions contain about 1 part percarboxylic acid for every about 1 part carboxylic acid after perhydrolysis, or about 6 part percarboxylic acid for every about 1 part carboxylic acid after perhydrolysis. In some embodiments, the compositions are free of or substantially free of carboxylic acids after the perhydrolysis reaction.

Alkalinity Source

The compositions also include a source of alkalinity. The source of alkalinity can include, but is not limited to, an alkaline metal hydroxide, an alkaline earth metal hydroxide, an alkali metal silicate, an alkali metal carbonate, borates and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. In other embodiments, an alkali metal carbonate can be used as a source of alkalinity. For example, in some embodiments, sodium carbonate, sodium bicarbonate or mixtures and derivatives thereof can be used.

The source of alkalinity can be present in the compositions in an amount sufficient to provide the desired pH. In some embodiments, the compositions have a pH greater than about 12, greater than about 12.5, or greater than about 13. In some embodiments, the alkaline source is present in the composition from about 0.001 wt-% to about 50 wt-%, from about 1 wt-% to about 30 wt-%, or about 10 wt-% to about 25 wt-%. In some embodiments, the alkaline source is present at from about 25 wt-% to about 50 wt-% of the composition. It is to be understood that all ranges and values between these ranges and values are encompassed by the present disclosure.

Oxidizing Agent

The compositions also include an oxidizing agent. The oxidizing agent may include a peroxide source. Oxidizing agents suitable for use with the compositions include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]6H_2O$ (also called sodium perborate tetrahydrate); sodium peroxyborate tetrahydrate of the formula $Na_2B_2(O_2)_2[(OH)_4].4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

In some embodiments, the oxidizing agent includes hydrogen peroxide, or a source or donor of hydrogen peroxide. In other embodiments, the oxidizing agent includes a peroxide source selected from a percarbonate, a perborate urea hydrogen peroxide, PVP-peroxides and mixtures thereof.

The compositions may contain an effective amount of an oxidizing agent. In some embodiments, the compositions include about 0.001 wt-% to about 60 wt-% of the oxidizing agent, or about 1 wt-% to about 25 wt-% of the oxidizing agent. In some embodiments, the compositions include about 30 wt-% to about 50 wt-% of the oxidizing agent. It is to be understood that all ranges and values between these ranges and values are encompassed by the present invention.

Solvent

In some embodiments, the compositions of the invention further include a solvent. In some embodiments, the solvent is water. The water may be provided by the use of aqueous reagents, viz. oxidizing agent, alkalinity source. In other embodiments, an additional amount of water is added to the compositions. The compositions may be free of or substantially free of any added water. A non-aqueous solvent may also be used in the compositions. For example, in some embodiments, an alcohol is included as a solvent in the compositions.

The compositions may include an effective amount of solvent. In some embodiments, the compositions may include about 10 wt-% to about 99 wt-% of a solvent, or about 20 wt % to about 80 wt-% of a solvent. In other embodiments, the compositions may include more than about 30 wt-%, more than about 50 wt-%, more than about 60 wt-% or more than 70% of a solvent. It is to be understood that all values and ranges between these values and ranges are encompassed by the present invention.

Eliminated Functional Ingredients

Unlike conventional equilibrium based peroxycarboxylic acid compositions, the compositions disclosed herein are formed from a non-equilibrium reaction. Further, the composition disclosed herein can be used immediately after generation. Thus, many of the additional ingredients required in equilibrium based compositions do not need to be included in the present compositions. In some embodiments stabilizing agents are preferred for certain compositions according to the invention and provide benefits. However, beneficially, the use of non-equilibrium chemistry according to the present invention optionally provides that the compositions can be free of, or substantially free of a stabilizing agent.

Stabilizing agents are commonly added to equilibrium peroxycarboxylic acid compositions to stabilize the peracid and hydrogen peroxide and prevent the decomposition of these constituents within the compositions. Various embodiments of the invention do not require the use of at least one or more of such stabilizing agents. Examples of stabilizing agents may include for example, surfactants, couplers, hydrotropes, acid catalysts and the like that are conventionally used in equilibrium peracid compositions to stabilize and improve shelf life of the composition.

Further examples of stabilizing agents include, for example, chelating agents or sequestrants. Such sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid). Dipicolinic acid, 1-hydroxy ethylidene-1,1-diphosphonic acid (CH3C(PO3H2) 2OH) (HEDP) are further example of stabilizing agents.

Additional examples of stabilizing agents commonly used in equilibrium chemistry to stabilize the peracid and hydrogen peroxide and/or prevent the premature oxidation of the composition include phosphonic acid or phosphonate salt. Phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are well known as used stabilizing agents.

Exemplary commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), (N[CH$_2$PO$_3$H$_2$]$_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM. Further exemplary sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N, N-diacetic acid; and the like; and mixtures thereof. Still further sequestrants include polycarboxylates, including, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

Further, unlike conventional equilibrium based peroxycarboxylic acid compositions, the present compositions can also be free of, or substantially free of surfactants. This is especially advantageous for compositions incorporating C5 to C18 peroxycarboxylic acids. That is, under perhydrolysis conditions, the C5-C18 peroxycarboxylic acid anions generated are water soluble. If the anions (e.g. peroxycarboxylic acid-forming compositions) are acidified for end use applications, the concentrations of peroxycarboxylic acids are below the water solubility limit of the peroxycarboxylic acids. Thus, couplers are not needed to couple the peroxycarboxylic acids in solution.

Additional Functional Ingredients

The compositions may also include additional functional ingredients. Additional functional ingredients suitable for use in the present compositions include, but are not limited to, acidulants, hydrotropes, dispersants, antimicrobial agents, optical tracers, solidification agent, aesthetic enhancing agent (i.e., colorant (e.g., pigment), odorant, or perfume), among any number of constituents which can be added to the composition. For example, suitable functional ingredients for various embodiments of the invention are hydrotropes, which may be desired for producing clear compositions or dispersants which are more efficient in producing homogeneous dispersions. Such adjuvants can be preformulated with the present compositions or added to the compositions after formation, but prior to use. The compositions can also contain any number of other constituents as necessitated by the application, which are known and which can facilitate the activity of the present compositions.

Acidulant

In an embodiment, the present compositions can include an acidulant. The acidulant can be added to the compositions after the formation of the percarboxylic acid. That is, an acidulant can be added to the peroxycarboxylic acid concentrate to form an acidified use solution. The acidulant can be effective to form a use composition with pH of about 1 or less. The acidulant can be effective to form a use composition with pH of about 8, about 8 or less, about 7, about 7 or less, about 6, about 6 or less, about 5, about 5 or less, or the like. In some embodiments, the acidulant is present at an amount effective to form a use solution with a pH of about 6 to about 8, about 1 to about 8, or about 1 to about 5. In a further embodiment, the acidulant may be added to a semi-diluted reaction solution to produce meta-stable peracid composition.

Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In an embodiment, the acidulant includes a carboxylic acid with $pK_a$ less than 5. Suitable carboxylic acids with $pK_a$ less than 5 include acetic acid, hydroxyacetic acid, hydroxypropionic acid, other hydroxycarboxylic acids, mixtures thereof, or the like. Such an acidulant is present at a concentration where it does not act as a solubilizer. In some embodiments, the compositions are free of, or substantially free of a carboxylic acid.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

Premix Formulations

In an embodiment, the reagents described herein (e.g. at least one ester of a polyhydric alcohol and a carboxylic acid, source of alkalinity, oxidizing agent) may be combined into various premix formulations to reduce the number of raw starting materials required for the methods and compositions and further simplify the methods of the invention. According to such an embodiment the providing of premix formulations ensures consistent and stable delivery of reagents.

Premix formulations suitable for use according to the invention may comprise, consist of and/or consist essentially of at least one ester, an oxidizing agent and mixtures thereof. Premix formulations suitable for use according to the invention may comprise, consist of and/or consist essentially of at least one ester, an oxidizing agent, a solvent and mixtures thereof. Premix formulations suitable for use according to the invention may also comprise, consist of and/or consist essentially of at least one ester, an oxidizing agent, water, solvents, dispersing agents, and mixtures thereof.

As one skilled in the art will ascertain the use of premixes employs additional function ingredients for purpose of stabilizing the premix concentrate for use in the compositions and methods according to the invention. For example, hydrotropes, dispersing agents and/or other solvents may be desirable for maintaining the solubility and stability of a particular concentrated premix. The use of any couplers or dispersing agent (such as a surfactant) within a premix formulation is distinct from the use of surfactants in the conventional generation and storage of peracid chemistries, wherein couplers are critical to establishing and maintaining a stable, clear solution of the generated peracid chemistry.

According to the invention, the use of dispersing agents alone within a concentrated premix formulation does not stabilize the premix composition. Rather the dispersing agents are provided in an amount suitable for providing meta-stable peracid compositions generated from the premix after acidification, before further dilution for application. The most efficient dispersing agents were found to be anionic surfactants, and this type of surfactant is known to have high foaming profile. For applications which involves mechanical actions (e.g. CIP sanitizing), the high foam property of the composition is undesirable. Thus, in addition to economic reason, it is preferred to use a minimum amount of the dispersing agent to achieve a meta-stable peracid composition to meet the application of use requirements.

According to an embodiment of the invention less than about 10 ppm, preferably less than about 9 ppm, less than about 8 ppm, less than about 7 ppm, less than about 6 ppm, less than about 5 ppm, less than about 4 ppm, less than about 3 ppm, less than about 2 ppm, or less than about 1 ppm of a dispersing agent is included in the generated peracid chemistry as a result of the use of a surfactant dispersing agent in a concentrated premix formulation according to the invention. This is distinct from the level of surfactants in use solutions of a traditional peracid chemistry, where the amounts of surfactants are normally in excess of about 50 ppm, in excess of about 60 ppm, in excess of about 70 ppm, in excess of about 80 ppm, in excess of about 90 ppm, or in excess of about 100 ppm.

According to a further embodiment of the invention less than about 2% dispersing agent is present in the premix composition, wherein at least about 5%, about 6%, about 7%, about 8% or about 9% are required to provide the stable, clear solution of a generated peracid chemistry when acidified. This is distinct from the generated peracid chemistry according to the invention wherein a meta stable chemistry is generated. Although not wishing to be limited to a particular theory of mechanism of action of the invention, the generated meta-stable composition is a milky colored composition having stability for at least a few hours.

According to an embodiment of the invention, the use of a solvent (e.g. ethanol) is an efficient way to make a stable premix composition. Solvents suitable for the concentrated premix formulations according to the invention include, for example, organic solvents such as alcohol, ether or ketone. Preferably, the solvent is a water soluble alcohol, such as ethanol, methanol, propanol, isopropanol and/or butanol. As one skilled in the art will ascertain the various isomers of the solvents, including alcohols, are further included within the scope of the solvents suitable for use with the concentrated premix formulations of the invention.

Beneficially, the use of concentrated premix formulation still does not require the use of any chelators and/or stabilizers. As a result, regardless of whether individual reagents or concentrated premix formulations are utilized according to the invention, both the reagents and the peracid compositions generated according to the invention provide sustainable chemistries as a result of the elimination of the use of various stabilizers and/or additional amounts of chemistry required to drive the formation of traditional peracid chemistry. As a result of reduced input of reagents for the compositions according to the invention (e.g. resulting from the use of a non-equilibrium reaction) there is a significantly reduced waste stream (e.g. any reagents and/or percentage of composition not impacting the micro-efficacy of the compositions). Instead the present invention provides increased amounts of post-reaction products (e.g. peracids) with decreased amounts of unreacted reagents.

In an aspect of the invention, a premix formulation may deliver the ester of a polyhydric alcohol and a carboxylic acid and the oxidizing agent. In one aspect a premix formulation includes an ester of a polyhydric alcohol and a carboxylic acid, an oxidizing agent and a dispersing agent. In another aspect a premix formulation includes an ester of a polyhydric alcohol and a carboxylic acid, an oxidizing agent, a dispersing agent and water.

Suitable dispersing agents for use according to the concentrated premix formulations of the invention include polymers, surface active agents or any compounds which will help to achieve a meta-stable solution after the ester perhydrolysis through the interaction with the peroxy fatty acids generated through perhydrolysis. These may include, for example, sulfonated oleic acids (SOA), 1-octanesulfonic acid (NAS), sodium lauryl sulfonates (SLS) and the like. In another aspect a premix formulation includes an ester of a polyhydric alcohol and a carboxylic acid, an oxidizing agent and a solvent. Ethanol and methanol are examples of suitable solvents for use in stabilizing the concentrated premix formulation according to the invention. The use of the solvent in certain embodiments obviates the use of a dispersing agent for premix stability. However, in alternative embodiments a premix formulation may include an ester of a polyhydric alcohol and a carboxylic acid, an oxidizing agent, a dispersing agent and a solvent. Without wishing to be limited to a particular theory or mechanism of action of the invention, the combined use of a dispersing agent and a solvent within a concentrated premix formulation reduces the overall need for a surfactant dispersing agent in the premix composition.

In still another aspect a concentrated premix formulation includes an oxidizing agent and a dispersing agent.

In certain embodiments, the concentrated premix composition includes about 0.001 to about 90 wt-% ester of the polyhydric alcohol and a carboxylic acid, about 0.1 to about 90 wt-% ester, about 1 to about 75 wt-% ester, about 10 to about 75 wt-% ester, about 25 to about 75 wt-% ester, about 30 to about 70 wt-% ester, or about 30 to about 65 wt-% ester.

In certain embodiments, the concentrated premix composition further includes about 0.001 to about 99 wt-% oxidizing agent, about 0.1 to about 95 wt-% oxidizing agent, about 1 to about 90 wt-% oxidizing agent, about 2.5 to about 60 wt-% oxidizing agent, about 5 to about 50 wt-% oxidizing agent, or about 10 to about 40 wt-% oxidizing agent.

In certain embodiments, the concentrated premix composition further includes about 0.001 to about 50 wt-% dispersing agent, about 0.1 to about 40 wt-% dispersing agent, about 1 to about 30 wt-% dispersing agent, about 5 to about 30 wt-% dispersing agent, about 5 to about 20 wt-% dispersing agent, or about 5 to about 15 wt-% dispersing agent. The amount of dispersing agent is selected to ensure that only enough dispersing agent to obtain a meta-stable solution after perhydrolysis and acidification. Beneficially according to the invention, the premix formulations do not contain sufficient dispersing agent to obtain a one phase premix solution.

In certain embodiments, the concentrated premix composition further includes about 0.001 to about 80 wt-% solvent, about 0.1 to about 40 wt-% solvent, about 1 to about 30 wt-% solvent, about 5 to about 30 wt-% solvent, about 5 to about 20 wt-% solvent, or about 5 to about 15 wt-% solvent. The level of solvent is selected to ensure the sufficient amount to solubilize the ester(s) of polyhydric alcohol in the concentrated premix formulation. As one skilled in the art will ascertain the amount of solvent required for such solubilization will vary depending upon the type and level of ester(s) in the premix composition.

In certain embodiments, the concentrated premix composition further includes about 0.001 to about 90 wt-% water, about 0.1 to about 80 wt-% water, about 1 to about 75 wt-% water, about 5 to about 60 wt-% water, about 10 to about 50 wt-% water, or about 20 to about 40 wt-% water. The premix compositions can include any of these ranges or amounts, including those not modified by about.

The pH of the concentrated premix formulation according to the invention is preferably between 2 and about 10, preferably between about 3 and about 9, and more preferably between about 5 and about 7. Thereafter the pH of the premix formulation is combined with an a source of alkalinity to increase the pH to a pH greater than about 12, greater than about 12.5, or greater than about 13 according to the invention.

Methods for Making, Using Individual Reagents

In some aspects, the present disclosure provides methods for making the peroxycarboxylic acid compositions disclosed herein. The method includes combining at least one ester of a polyhydric alcohol and a C1 to C18 carboxylic acid, a source of alkalinity and an oxidizing agent. This reaction mixture allows for the perhydrolysis of the ester to form the corresponding C1 to C18 peroxycarboxylic acid. Without wishing to be bound by any particular theory it is thought that the anion of the oxidizing agent (e.g. perhydroxide anion) present perhydrolyzes the ester bonds, thereby forming the corresponding percarboxylic acids.

In some embodiments, the pH of the reaction mixture is greater than about 12. In other embodiments, the reaction mixture is greater than about 12.5, or greater than about 13. The reagents can be combined in any suitable manner. Exemplary systems and methods for making the compositions are described in further detail in U.S. patent application Ser. Nos. 61/427,951 and 13/330,915, entitled Sugar Ester Peracid On-Site Generator and Formulator, U.S. patent application Ser. No. 13/330,981, entitled Continuous On-Line Adjustable Disinfectant/Sanitizer/Bleach Generator, and U.S. patent application Ser. No. 13/331,385, entitled Water Temperature as a Means of Controlling Kinetics of Onsite Generated Peracids, each filed concurrently herewith and incorporated by reference. For example, the reagents can be sequentially added to a reaction vessel, and mixed for an amount of time effective to form the desired percarboxylic acid concentration. Alternatively, the reagents can be added substantially simultaneously to a reaction vessel, and mixed for an amount of time effective to form the desired percarboxylic acid concentration. In some embodiments, the reagents are mixed for about 5 to about 30 minutes. In other embodiments, the reagents are mixed for about 10, about 15, about 20, or about 25 minutes.

In some embodiments, a mixed percarboxylic acid composition is formed by using more than one ester of a polyhydric alcohol and a C1 to C18 carboxylic acid as starting reagents and/or more than form of an ester of a polyhydric alcohol and a C1 to C18 carboxylic acid as starting reagents (e.g. mono, di, tri or mixtures thereof for ester formations). For example, in some embodiments, a mixed percarboxylic acid composition including peracetic acid and peroctanoic acid is formed. To form this composition, an ester of a polyhydric alcohol and a C2 carboxylic acid is combined with an ester of a polyhydric alcohol and a C8 carboxylic acid, a source of alkalinity, and an oxidizing agent.

When forming a mixed peracid composition, the order of addition can be varied depending on the reaction conditions. For example, in some embodiments, all of the reagents can be combined and mixed in one step. Alternatively, in some embodiments, one of the esters can be added to a reaction vessel, with an oxidizing agent, and a source of alkalinity added sequentially. This mixture can be allowed to react for an effective amount of time, prior to the second ester being added to the reaction mixture. Preparing the mixed percarboxylic acid system in a stepwise manner also allows for control of the reaction temperature. For example, by splitting the perhydrolysis reactions into two steps, the overall temperature of the reaction mixture is lower.

The order of addition and time for reaction can be varied according to the desired percarboxylic acid composition. That is, the reaction can be controlled so as to favor the reaction conditions for formation of each of the percarboxylic acids individually. For example, if it is known that one of the esters has a kinetically slower perhydrolysis reaction rate, that ester can be added to the reaction vessel first. After an amount of time sufficient to maximize the percarboxylic acid formation of the first ester, the second ester with a kinetically faster perhydrolysis reaction rate can be added to the reaction vessel.

The order of mixing and addition of reagents can be used to control the production of the percarboxylic acid composition, namely to ensure a consistent output of chemistry without any fouling (e.g. precipitation) of the reagents. In one aspect of the invention, the source of alkalinity (e.g. sodium hydroxide or caustic soda) is combined with water (e.g. diluted) prior to the addition of the ester source.

The concentration of reagents, in addition to mixing order, can further be used to control the production of the percarboxylic acid composition. In a preferred embodiment, the concentration of the source of alkalinity is diluted to produce a consistent output of chemistry without any fouling (e.g. precipitation) of the reagents. In one aspect the concentrated alkaline solution (e.g. NaOH) is diluted with a water source before the ester component is combined with the reagents. Although not intending to be limited according to any theory of the invention and/or mechanism of action, the invention demonstrates superior chemistry generation when a system delivers a source of alkalinity (e.g. NaOH solution) that is no more than about 50%, preferably no more than about 40% on an actives basis before combining with the ester reagent to initiate the peracid production reaction.

In some aspects, the present disclosure provides methods for forming an antimicrobial and/or disinfecting composition. The methods include providing a mixed peroxycarboxylic acid forming composition. The mixed peroxycarboxylic acid forming composition includes: a first ester of a polyhydric alcohol and a C1 to C18 carboxylic acid, for example a C1 to C4 carboxylic acid; a second ester of a polyhydric alcohol and a C1 to C18 carboxylic acid, for example a C8 to C11 carboxylic acid; a source of alkalinity; and an oxidizing agent. After allowing the reaction mixture to react for a sufficient amount of time, a mixed percarboxylic acid composition is formed. The mixed peroxycarboxylic acid composition is diluted with an acidic aqueous solution. In some embodiments, the mixed peroxycarboxylic acid composition is diluted with an amount of an acidic aqueous solution effective to provide the diluted composition with a pH of about 1.0 to about 8.0. In other aspects, the present disclosure provides methods for forming a composition including a single percarboxylic acid. The methods include providing a peroxycarboxylic acid forming composition. The composition includes: an ester of a polyhydric alcohol and a C1 to C18 carboxylic acid; a source of alkalinity; and an oxidizing agent, wherein said composition has a pH greater than 12. The peroxycarboxylic acid forming composition is then diluted with an acidic aqueous solution. In some embodiments, the diluted acidic peroxycarboxylic acid composition has a pH of about 1.0 to about 8.0.

Any acidic solution can be used to dilute the peroxycarboxylic acid compositions. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In an aspect the acid or acidic solution acidifies the peroxycarboxylic acid forming composition to the peroxycarboxylic acid composition. In a further aspect, the use of an acid or acidic solution dilutes the peroxycarboxylic acid compositions. Methods employing the acidification of the peroxycarboxylic acid forming composition further stabilize the composition. However, as one skilled in the art will appreciate, some reaction intermediates of the peroxycarboxylic acid forming composition are stable for sufficient periods of time and do not need to be acidified immediately. For example, some reaction intermediates are stable for at least 24 hours and can be utilized in an on-site application without the acidification step for further dilution and/or stabilization. Other peroxycarboxylic acid forming compositions are less stable and the perhydrolysis reaction requires quenching with the acid or acidic aqueous solution to lower the pH and stabilize more promptly.

In another aspect of the invention, the peroxycarboxylic acid forming compositions are acidified within a cleaning application or within a use system (i.e., post generator within a customer's process). For example, post-generator acidification may include a clean in place (CIP) process where the peroxycarboxylic acid forming composition is pumped to a temporary holding tank for use in a CIP system, or pumped directly to a CIP system where the acid is added either in a pipe or the CIP vessel itself. A further example of post-generator acidification may include a healthcare application or certain laundry applications where the acid is added to provide a peroxycarboxylic acid (with an acid pH) to provide bleaching and/or sanitizing benefits of the peracid.

According to additional embodiments of the invention, there are various applications for the compositions of the invention where acidification is not required and/or desired as the use of the peroxycarboxylic acid forming composition (anion solution) is preferred. For example, in a laundry application the acid is not be added in order to benefit from the alkaline pH of the anion for bleaching purposes. The alkaline pH for bleaching is obtained from the anion species, as a result the peroxycarboxylic acid forming composition does not have to be quenched with acid.

Methods for Making, Using Concentrated Premix Formulations

In additional aspects, the present disclosure provides methods for making the peroxycarboxylic acid compositions disclosed herein using concentrated premix formulations. Without limiting the scope of the invention and the methods for making the compositions disclosed herein, the same methods of making can be employed utilizing various concentrated premix formulations to combine the at least one ester of a polyhydric alcohol and a C1 to C18 carboxylic acid, a source of alkalinity and an oxidizing agent. The use of concentrated premix formulations minimizes the number of composition reagents according to the invention to simplify the methods even further.

The use of various concentrated premix formulations according to the invention does not alter the remaining method steps—only the input of the reagents into a system using the methods of the invention. Upon combining a particular concentrated premix formulation with the remaining reagents the reaction mixture allows for the perhydrolysis of the ester to form the corresponding C1 to C18 peroxycarboxylic acid. Without wishing to be bound by any particular theory it is thought that the oxidizing agent present (e.g. hydrogen peroxide or its anion) perhydrolyzes the ester bonds, thereby forming the corresponding percarboxylic acids.

According to an exemplary method of making the peroxycarboxylic acid compositions, a concentrated premix formulation comprising the ester(s) and oxidizing agent are mixed with the alkalinity source to form concentrated peracid chemistry. As disclosed herein, the alkalinity source may be an alkaline solution (e.g. NaOH) that is diluted with a water source before the concentrated premix comprising the ester component is combined with the dilute alkaline source.

The generated concentrated peracid chemistry according to the invention, regardless of whether generated using individual reagent sources and/or concentrated premix formulations, remains stable from a few hours to a few days. The on-site generated according to the invention obviates the need of various stabilizing agents as the chemistry is used on-site and not shipped and/or maintained in storage for any significant period of time.

The generated concentrated peracid chemistry may be diluted according to a particular use. For example, in an embodiment, the concentrated peracid chemistry is added to a post dilution tank or reservoir where water may be used to dilute the concentrated chemistry. This step may be referred to as generating an intermediate dilution. Without being limited to a particular theory of the invention, the dilution of the concentrated chemistry into an intermediate dilution in an alkaline solution maintains the phase stability of the peracid chemistry. In one aspect the solution may be diluted to about 100 ppm to about 10,000 ppm solution, preferably to about 1,000 ppm to about 4,000 ppm, and more preferably to about 1,000 ppm solution (e.g. about 0.1% active peracid). Thereafter the acidification of the diluted peracid chemistry may take place without any fouling of the chemistry. Thereafter the diluted peracid chemistry may be sourced to various use applications at very dilute amounts as a result of the on-site generation. For example, diluted peracid chemistry may be added into a use solution with concentrations less than about 10 ppm, less than about 50 ppm or less than about 100 ppm, without the wasteful shipment of such diluted chemistries.

As one skilled in the art will ascertain the method of making the peracid compositions, in particular the various dilutions of the concentrated peracid chemistries and/or acidification steps, may not be required depending upon the particular use applications of the chemistry. For example, a non-limiting example includes the use of a concentrated peracid chemistry for certain textile and/or bleaching applications. In such an embodiment, the concentrated peracid chemistry does not require the dilution in an alkaline solution to an intermediate solution having an active chemistry concentration of from about 100 ppm to about 10,000 ppm. Rather the concentrated alkaline chemistry could be immediately sourced to an application of use (e.g. textile cleaning and/or bleaching).

ILLUSTRATED EMBODIMENTS

Figure 2:
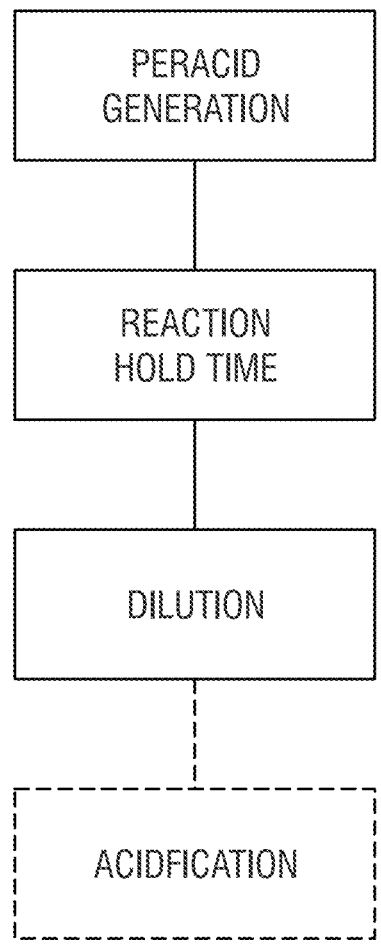
FIG. 2 shows a diagram of an embodiment of methods of making the peracid chemistry according to the invention.

FIG. 2 shows a diagram of an embodiment of certain methods of making the peracid chemistry according to the invention. As set forth therein, the methods of making the compositions include peracid generation which occurs through the dosing (e.g. injection) of raw starting materials (e.g. reagents) into a reaction vessel. The particular apparatuses and/or systems for the production of the chemistry are disclosed in the related applications set forth in the Cross Reference to Related Applications, which are incorporated herein by reference. In particular, the alkalinity source and water may be initially combined to obtain a diluted caustic source. According to a preferred embodiment, the caustic is diluted to a concentration of less than or equal to about 20% by weight. Thereafter, the ester and oxidizing source are combined with the diluted caustic for the perhydrolysis reaction to take place and generate the peracid composition. Thereafter, the reagents are held for the reaction to go to completion for a sufficient period of time. The next step involves the dilution of the concentrated peracid chemistry. In a further aspect the diluted chemistry can be acidified using an acid or aqueous acid solution.

Methods for Using

In some aspects, the present disclosure includes methods of using the peroxycarboxylic acid forming compositions disclosed herein. In some aspects, the methods of using the compositions employ a chemistry having a pH of from about 0 to about 5 for various antimicrobial and/or bleaching applications. In other aspects, the methods of using the compositions employ a chemistry having a pH of from about 5 to about 9 for various antimicrobial and/or bleaching applications. In still further aspects, the methods of using the compositions employ a chemistry having a pH of from about 5 to about 14 for various bleaching applications.

In some embodiments, these methods employ the antimicrobial and/or bleaching activity of the compositions. For example, the invention includes a method for reducing a microbial population, a method for reducing the population of a microorganism on skin, a method for treating a disease of skin, a method for reducing an odor, and/or a method for bleaching. These methods can operate on an article, surface, in a body or stream of water or a gas, or the like, by contacting the article, surface, body, or stream with the compositions. Contacting can include any of numerous methods for applying the compositions, such as spraying the compositions, immersing the article in the compositions, foam or gel treating the article with the compositions, wiping the composition or a combination thereof.

In some aspects, the compositions are present at an amount effective for killing one or more of the food-borne pathogenic bacteria associated with a food product, including, but not limited to, *Salmonella typhimurium, Salmonella javiana, Campylobacter jejuni, Listeria monocytogenes*, and *Escherichia coli* O157:H7, yeast, and mold. In some embodiments, the compositions are present at an amount effective for killing one or more of the pathogenic bacteria associated with a health care surfaces and environments including, but not limited to, *Salmonella typhimurium, Staphylococcus aureus*, methicillin resistant *Staphylococcus aureus, Salmonella choleraesurus, Pseudomonas aeruginosa, Escherichia coli*, mycobacteria, yeast, and mold. The compositions of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions, as described above, have activity against a wide variety of human pathogens. The present compositions can kill a wide variety of microorganisms on a food processing surface, on the surface of a food product, in water used for washing or processing of food product, on a health care surface, or in a health care environment.

The compositions can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compositions can be employed as a foaming or nonfoaming environmental sanitizer or disinfectant.

The compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people. The compositions can also be employed as an antimicrobial teat dip.

In some aspects, the compositions obtained according to the methods and apparatus of the present invention can be employed for reducing the population of pathogenic microorganisms, such as pathogens of humans, animals, and the like. The compositions exhibit activity against pathogens including fungi, molds, bacteria, spores, and viruses, for example, *S. aureus, E. coli, Streptococci, Legionella, Pseudomonas aeruginosa, mycobacteria, tuberculosis*, phages, or the like. Such pathogens can cause a variety of diseases and disorders, including mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The compositions can also be used to treat waste water where both its antimicrobial function and its oxidant properties can be utilized. Aside from the microbial issues surrounding waste water, it is often rich in malodorous compounds of reduced sulfur, nitrogen or phosphorous. A strong oxidant such as the present invention converts these compounds efficiently to their odor free derivatives e.g. the sulfates, phosphates and amine oxides. These same properties are very useful in the pulp and paper industry where the property of bleaching is also of great utility.

In some aspects, the compositions of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the compositions can be employed include a milk line dairy, a continuous brewing system, food processing lines such as pumpable food systems and beverage lines, etc. Food service wares can be disinfected with the compositions. For example, the compositions can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like. The composition can also be used in treating microbes found in aqueous systems associated with petroleum or LP gas recovery or fermentation processes and pulp and paper processes and the like.

A filter containing peracid compositions of the present invention can reduce the population of microorganisms in air and liquids. Such a filter can remove water and air-borne pathogens such as *Legionella*.

The compositions obtained according to the methods and apparatus of the present invention can be employed for reducing the population of microbes, fruit flies, or other insect larva on a drain or other surface.

The compositions can also be employed by dipping food processing equipment into the use solution, soaking the equipment for a time sufficient to sanitize the equipment, and wiping or draining excess solution off the equipment, The compositions may be further employed by spraying or wiping food processing surfaces with the use solution, keeping the surfaces wet for a time sufficient to sanitize the surfaces, and removing excess solution by wiping, draining vertically, vacuuming, etc.

The compositions may also be used in a method of sanitizing hard surfaces such as institutional type equipment, utensils, dishes, health care equipment or tools, and other hard surfaces. The compositions of the present invention can also be used for laundry or textile applications. The compositions can be employed by rinsing laundry or textile surfaces with the use solution, keeping the surfaces wet for a sufficient time to wash, destain, sanitize, bleach and/or rinse the surface.

A concentrate or use concentration of the compositions can be applied to or brought into contact with an object by any conventional method or apparatus for applying an antimicrobial or cleaning compound to an object. For example, the object can be wiped with, sprayed with, foamed on, and/or immersed in the compositions, or a use solution made from the compositions. The compositions can be sprayed, foamed, or wiped onto a surface; the compositions can be caused to flow over the surface, or the surface can be dipped into the compositions. Contacting can be manual or by machine. Food processing surfaces, food products, food processing or transport waters, and the like can be treated with liquid, foam, gel, aerosol, gas, wax, solid, or powdered stabilized compositions according to the invention, or solutions containing these compounds.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include the internal components of tanks, lines, pumps and other process equipment used for processing typically liquid product streams such as beverages, milk, juices.

A method of sanitizing substantially fixed in-place process facilities includes the following steps. A composition in accordance with various embodiments of the invention is introduced into the process facilities at a temperature in the range of about 4° C. to 60° C. After introduction of the composition, the solution is held in a container or circulated throughout the system for a time sufficient to sanitize the process facilities (e.g., to kill undesirable microorganisms). After the surfaces have been sanitized by means of the present compositions, the solution is drained. Upon completion of the sanitizing step, the system optionally may be rinsed with other materials such as potable water. The compositions can be circulated through the process facilities for 10 minutes or less.

The present methods can include delivering the present composition via air delivery to the clean-in-place or other surfaces such as those inside pipes and tanks. This method of air delivery can reduce the volume of solution required.

Methods for Contacting a Food Product

In some aspects, the present invention provides methods for contacting a food product with compositions according to the invention employing any method or apparatus suitable for applying such compositions. For example, in some embodiments, the food product is contacted by the compositions with a spray of the compositions, by immersion in the compositions, by foam or gel treating with the compositions. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the compositions of the present invention to other objects.

The present methods require a certain minimal contact time of the compositions with food product for occurrence of significant antimicrobial effect. The contact time can vary with concentration of the use compositions, method of applying the use compositions, temperature of the use compositions, amount of soil on the food product, number of microorganisms on the food product, type of antimicrobial agent, or the like. The exposure time can be at least about 5 to about 15 seconds. In some embodiments, the exposure time is about 15 to about 30 seconds. In other embodiments, the exposure time is at least about 30 seconds.

In some embodiments, the method for washing a food product employs a pressure spray including compositions of the present invention. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing microorganisms, perhaps due to better exposure of the solution into the crevasses or small colonies containing the micro-organisms. The spray solution, before application, can also be heated to a temperature of about 15 to 20° C., for example, about 20 to 60° C. to increase efficacy. The spray stabilized compositions can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed compositions to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compounds of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in the liquid compositions of the present invention can be accomplished by any of a variety of methods known to those of skill in the art. For example, the food product can be placed into a tank or bath containing the compositions. Alternatively, the food product can be transported or processed in a flume of the compositions. The washing solution can be agitated to increase the efficacy of the solution and the speed at which the solution reduces microorganisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the compositions can be rinsed, drained, or evaporated off the food product.

In other embodiments, a food product can be treated with a foaming version of the compositions of the present invention. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, including, for example, alkyl aryl sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In some embodiments, a food product can be treated with a thickened or gelled version of the compositions of the present invention. In the thickened or gelled state the washing solution remains in contact with the food product surface for longer periods of time, thus increasing the antimicrobial efficacy. The thickened or gelled solution will also adhere to vertical surfaces. The compositions can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Methods for Beverage, Food, and Pharmaceutical Processing

The compositions of the present invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The compositions of the present invention can be used to sanitize, disinfect, act as a sporicide for, or sterilize bottles, pumps, lines, tanks and mixing equipment used in the manufacture of such beverages. Further, the compositions of the present invention can be used in aseptic, cold filling operations in which the interior of the food, beverage, or pharmaceutical container is sanitized or sterilized prior to filling. In such operations, a container can be contacted with the compositions, typically using a spray, dipping, or filling device to intimately contact the inside of the container with the compositions, for a sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacteria of the genus *Bacillus* spp. can be a significant problem in bottling processes, particularly in cold aseptic bottling processes. The compositions of the present invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the compositions of the invention can be used to sanitize the interior of beverage containers prior to filling with the carbonated (or noncarbonated) beverage. Typical carbonated beverages in this application include, but are not limited to, cola beverages, fruit beverages, ginger ale beverages, root beer beverages, iced tea beverages which may be non-carbonated, and other common beverages considered soft drinks. The compositions of the invention can be used to sanitize both the tanks, lines, pumps, and other equipment used for the manufacture and storage of the soft drink material and also used in the bottling or containers for the beverages. In an embodiment, the compositions are useful for killing both bacterial and fungal microorganisms that can be present on the surfaces of the production equipment and beverage containers.

Methods for Industrial Processing

In some aspects, the invention includes methods of using the peroxycarboxylic acid forming compositions and/or peroxycarboxylic acids to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid forming compositions and/or peroxycarboxylic acids are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Biofuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A study was run to determine the ability to form peroxycarboxylic acids in situ from ester starting materials at alkaline pH levels. For this study, two different peroxycarboxylic acid forming compositions were each studied at two different pH levels. First, a peracetic acid (POAA) forming composition was tested at pH 12 and pH 13. For this test, 1.89 grams of hydrogen peroxide was mixed in a beaker with 0.62 grams of triacetin, 15 grams of distilled water, and 7.75 grams of a 10% solution of sodium hydroxide (NaOH). The beaker was fitted with a pH probe. After the sodium hydroxide was added the pH went up to about 12 immediately, and remained relatively stable while the sampling was performed. The peroxycarboxylic acid concentration was measured by removing a sample aliquot of the test solution, acidifying it with acetic acid, and titrating using an iodometric method. Both the peroxycarboxylic acid concentration and the hydrogen peroxide concentrations were measured over time. The above procedure was then repeated using an additional 11.71 grams of a 10% sodium hydroxide solution. This raised the pH to about 13 initially.

The above procedures were repeated twice using sorbitan caprylate instead of triacetin, to generate peroxyoctanoic acid (POOA) in situ. The peroxyoctanoic acid was also generated at both pH 12 and pH 13. The peroxycarboxylic acid concentration and hydrogen peroxide concentration of these test solutions was also measured over time. The results are shown in FIG. 1.

As can be seen in FIG. 1, the peroxyoctanoic acid generating solution was far more stable than the peracetic acid generating solution over time. This held true even for the elevated pH 13 test. Thus, as can be seen from this data, peroxyoctanoic acid can be generated in situ at relatively high pH levels, viz. pH about 13.

Example 2

A study was performed to evaluate the ability to generate a mixed peroxycarboxylic acid composition in situ from ester starting materials at alkaline pH. For this study, 1.28 grams of sorbitan octanoate, 14.68 grams of water, and 3.66 grams of a 35% hydrogen peroxide solution were added in a 100 mL beaker. With magnetic stirring, 14.64 grams of a 10% sodium hydroxide solution was added to the beaker. The solution was mixed for ten minutes. Then, 1.70 grams of triacetin was added to the solution. After mixing for an additional five minutes, the solution was sampled to measure the peroxyacetic (POAA) and peroxyoctanoic (POOA) acid concentrations.

This two-step addition process was also compared to a one step process. For the one step process, 1.26 grams of sorbitan octanoate, 1.70 grams of triacetin, 14.67 grams of water, and 3.66 grams of a 35% hydrogen peroxide solution were added in a 100 mL beaker. With magnetic stirring, 14.64 grams of a 10% sodium hydroxide solution was added to the beaker. After mixing for 15 minutes, the solution was sampled for POAA and POOA levels. The results for both the two step and the one step reaction methods are shown in the table below.

TABLE 1

| Reaction Process | Peroxyacetic Acid (wt-%) | Peroxyoctanoic Acid (wt-%) | Peroxyacetic/ Peroxyoctanoic (wt-% as Peroxyacetic acid) | Temperature (maximum) | pH (initial-end) |
|---|---|---|---|---|---|
| Two Step | 4.32 | 0.71 | 4.89 | 24.6° C. | 12.19-11.47 |
| One Step | 3.95 | 0.60 | 4.33 | 28.1° C. | 11.75-11.60 |

As can be seen from this table, the two step process delivered higher levels of POOA and POAA. It was also found that using the two step process described above generated lower temperatures than the one step process. These lower temperatures are important from both a safety and a stability standpoint for this reaction. Without wishing to be bound by any particular theory, it is thought that in the two step process, the kinetically slower perhydrolysis reaction of sorbitan octanoate was exposed to a more favorable perhydrolysis condition than in the one step reaction. That is in the two step process, the sorbitan octanoate is exposed to a higher pH and stoichiometrically more hydrogen peroxide. It is thought that these conditions contributed to the higher yield of POOA. Further, it is thought that the kinetically fast perhydrolysis reaction of triacetin was given enough perhydrolysis reaction time, but avoided a prolonged exposure to a high pH condition, and thus achieved a better POAA yield.

Example 3

A study was run to evaluate the ability to form a solid peroxycarboxylic acid forming composition. For this study, 2.5 grams of sorbitan octanoate was mixed with 2.5 grams of sodium bicarbonate in a beaker. Light sodium bicarbonate (2.5 grams) was then added. With stirring, the composition solidified quickly. Then, 2.5 grams of sodium percarbonate, and 1.04 grams of sodium hydroxide were added. The solid mixture was pressed in a mold with a 1.5 inch diameter, at a pressure of 2000 psi. A solid tablet was formed in one minute.

The solid was then added to 25 grams of deionized (DI) water, and stirred for 15 minutes. The solution was then sampled and measured for POOA concentration. The iodometric titration showed 1.08% POOA present in the solution. Thus, it was shown that a solid peroxycarboxylic acid forming composition can be generated in situ using an ester starting material.

Example 4

A study was run to evaluate the sanitizing efficacy of mixtures of peroxycarboxylic acids generated in situ from esters under alkaline conditions. For this study the following ester based peroxycarboxylic acid forming compositions were used.

TABLE 2

| Peroxyoctanoic Premix (POOA) | | Peroxyacetic Premix (POAA) | |
|---|---|---|---|
| Composition | Amount (g) | Composition | Amount (g) |
| Sorbitan octanoate | 2.50 | Triacetin | 4.90 |
| 35% Hydrogen Peroxide | 2.26 | 35% Hydrogen Peroxide | 10.58 |
| Water | 15.16 | Water | 42.31 |
| 10% NaOH | 10.74 | 10% NaOH | 42.21 |

The above Peroxycarboxylic acid premixes were then tested alone at various concentrations, and mixed at various concentrations against *Staphylococcus aureus* ATCC 6538, and *Escherichia coli* ATCC 11229. The compositions tested are shown in the table below.

TABLE 3

| Test Substance | Tested Concentration | Diluent | Test Solution (Volume of Test Substance/Total Volume) | pH |
|---|---|---|---|---|
| POOA | 13 ppm | 500 ppm Synthetic Hard Water (pH 7.80) | 0.18 g/300 g | 4.98 |
| POAA | 61 ppm | | 0.64 g/300 g | 5.00 |
| POOA + POAA | 13 ppm + 61 ppm | | 0.32 g + 1.07 g/500 g | 4.99 |
| POAA | 35 ppm | | 0.21 g/300 g | 5.00 |
| POOA | 15 ppm | | 0.37 g/300 g | 5.01 |
| | 20 ppm | | 0.45 g/300 g | 4.98 |
| POOA + POAA | 20 ppm + 15 ppm | | 0.45 g + 0.26 g/500 g | 4.99 |
| | 15 ppm + 35 ppm | | 0.35 g + 0.62 g/500 g | 5.01 |

The test substances were tested against *Staphylococcus aureus* ATCC 6538, and *Escherichia coli* ATCC 11229 at 25° C.±1° C. for 30 seconds. A neutralizer screen was performed as part of the testing to verify that the neutralizer adequately neutralized the product and was not detrimental to the tested organisms. The inoculum numbers are shown in the table below.

TABLE 4

| Test System | CFU/mL | $Log_{10}$ Growth | Average $Log_{10}$ growth |
|---|---|---|---|
| *Staphylococcus aureus* ATCC 6538, | $9.3 \times 10^7$ | 7.97 | 7.97 |
| | $9.5 \times 10^7$ | 7.98 | |
| *Escherichia coli* ATCC 11229 | $1.10 \times 10^8$ | 8.04 | 8.05 |
| | $1.17 \times 10^8$ | 8.07 | |

The results from the various test substances are shown in the tables below.

TABLE 5

*Staphylococcus aureus* ATCC 6538

| Test Substance | Exposure Time | Survivors (CFU/mL) | Average $Log_{10}$ Survivors | Log Reduction |
|---|---|---|---|---|
| 13 ppm POOA + 61 ppm POAA | 30 seconds | $1.0 \times 10^1$, $<1.0 \times 10^1$ | 1.00 | 6.97 |
| 20 ppm POOA + 15 ppm POAA | 30 seconds | $<1.0 \times 10^1$, $<1.0 \times 10^1$ | <1.00 | >6.97 |
| 15 ppm POOA + 35 ppm POAA | 30 seconds | $<1.0 \times 10^1$, $<1.0 \times 10^1$ | <1.00 | >6.97 |

TABLE 6

*Escherichia coli* ATCC 11229

| Test Substance | Exposure Time | Survivors (CFU/mL) | Average $Log_{10}$ Survivors | Log Reduction |
|---|---|---|---|---|
| 13 ppm POOA pH 4.98 | 30 seconds | $4.22 \times 10^7$, $3.52 \times 10^7$ | 7.59 | 0.46 |
| 61 ppm POAA pH 5.00 | 30 seconds | $3.0 \times 10^3$, $2.4 \times 10^4$ | 3.93 | 4.12 |
| 13 ppm POOA + 61 ppm POAA | 30 seconds | $<1.0 \times 10^1$, $<1.0 \times 10^1$ | <1.00 | >7.05 |

TABLE 6-continued

Escherichia coli ATCC 11229

| Test Substance | Exposure Time | Survivors (CFU/mL) | Average $Log_{10}$ Survivors | Log Reduction |
|---|---|---|---|---|
| pH 4.99 35 ppm POAA | 30 seconds | $1.85 \times 10^7$, $1.86 \times 10^7$ | 7.27 | 0.78 |
| pH 5.00 15 ppm POOA | 30 seconds | $1.06 \times 10^7$, $1.83 \times 10^7$ | 7.15 | 0.90 |
| pH 5.01 20 ppm POOA | 30 seconds | $7.0 \times 10^5$, $7.0 \times 10^5$ | 5.85 | 2.20 |
| pH 4.98 20 ppm POOA + 15 ppm POAA | 30 seconds | $<1.0 \times 10^1$, $<1.0 \times 10^1$ | <1.00 | >7.05 |
| 15 ppm POOA + 35 ppm POAA | 30 seconds | $<1.0 \times 10^1$, $<1.0 \times 10^1$ | <1.00 | >7.05 |

As can be seen from these results, at every concentration tested, POOA and POAA alone at pH 5.0 failed the sanitizer test with less than 5 log reductions of *Escherichia coli* after 30 seconds. A passing result for a sanitizing efficacy screen requires a greater than 5 log reduction in test system growth after a 30 second exposure time. However, a synergistic effect was observed between POOA and POAA when mixed together. For example a complete kill of both *Staphylococcus aureus* and *Escherichia coli* was observed after a 30 second exposure time with the mixed systems.

Example 5

A study was run to evaluate the ability to form peroxycarboxylic acids from ester starting materials in various solvents. First, a test was run to determine the ability to form a peroxycarboxylic acid (POOA) from glyceryl trioctanoate using water as the solvent. For this test, 2.50 grams of glyceryl trioctanoate was added to 2.25 grams of 35% hydrogen peroxide. Then, 30 grams of deionized water, and 10.50 grams of a 10% aqueous sodium hydroxide solution were added. All of these components were added in serial fashion to a 150 mL Pyrex beaker fitted with a magnetic stir bar. Just prior to the addition of the sodium hydroxide, stirring was initiated and maintained through all of the subsequent addition steps. Samples of the reaction solution were taken at 15, 27, and 40 minutes. The samples were treated with acetic acid, and titrated using an iodometric peroxycarboxylic acid titration to measure the peroxycarboxylic acid concentration. The results are shown in Table 7.

A comparative example was then run using a semi-methanolic reaction solution. For this comparative example, 2.50 grams of glyceryl trioctanoate was added to 2.25 grams of 35% hydrogen peroxide followed by 30 grams of 100% methanol, and 10.50 grams of a 10% aqueous sodium hydroxide solution. All of these components were added in serial fashion to a 150 mL Pyrex beaker fitted with a magnetic stir bar. Just prior to the addition of the sodium hydroxide, stirring was initiated and maintained through all of the subsequent steps. Samples of the reaction solution were taken at 10, 20, and 30 minutes and treated with acetic acid and titrated using a standard iodometric peroxycarboxylic acid titration. The results from this semi-methanolic reaction solution comparative example are also shown in Table 7.

Finally, another comparative example was run using a purely alcoholic reaction solution. For this comparative example, 2.50 grams of glyceryl trioctanoate was added to 6.75 grams of 10% urea-hydrogen peroxide-ethanol solution followed by 30 grams of 100% methanol, and 14.70 grams of a 10% potassium hydroxide/methanol solution. All of these components were added in serial fashion to a 150 mL Pyrex beaker fitted with a magnetic stir bar. Just prior to the addition of the potassium hydroxide solution, stirring was initiated and maintained through all of the subsequent steps. Samples of the reaction solution were taken at 8, 26, 47, and 69 minutes. The samples were treated with acetic acid, and titrated using a standard iodometric peroxycarboxylic acid titration to measure for peroxycarboxylic acid concentration. The results are also shown in Table 7 below.

TABLE 7

| Reaction Time (min) | Purely Aqueous Reaction Solution | | Semi-Methanolic Reaction Solution | | Pure Methanolic Reaction Solution | |
|---|---|---|---|---|---|---|
| | POOA (%) | Portion Converted (%) | POOA (%) | Portion Converted (%) | POOA (%) | Portion Converted (%) |
| 8 | | | | | 1.59 | 34.0 |
| 10 | | | 1.00 | 18.0 | | |
| 15 | 0.00 | 0.00 | | | | |
| 20 | | | 1.89 | 34.0 | | |
| 26 | | | | | 1.69 | 36.1 |
| 27 | 0.00 | 0.00 | | | | |
| 30 | | | 2.32 | 42.0 | | |
| 40 | 0.00 | 0.00 | | | | |
| 47 | | | | | 1.59 | 34.0 |
| 69 | | | | | 1.59 | 34.0 |

As can be seen from this table, in a purely aqueous reaction, no POOA was formed. Without wishing to be bound by any particular theory, it is thought that the HLB of glyceryl trioctanoate is too low (less than 3). That is, the low water solubility/dispersability of glyceryl trioctanoate prohibits the perhydrolysis reaction in the purely aqueous environment, regardless of the otherwise favorable perhydrolysis conditions. This surprising result is true for sugar esters in general with an HLB less than 3. For example, sorbitan trioctanoate (HLB less than 3) could not be perhydrolized in an aqueous solution to generate peroxyoctanoic acid, however, sorbitan monooctanoate (HLB greater than 3) was readily perhydrolysibile in aqueous solutions.

Example 6

A single peracid chemistry (POOA) was generated according to the invention using the reagents set forth in Table 8A. POOA production rates were generated as a function of reagents and generator temperatures. A continuous ABF generator was used wherein both the reagent and reaction vessels temperature were controlled with a heating/cooling water bath as set forth in Table 8B. The results demonstrate the POOA production as a function of time.

TABLE 8A

| Reagent Formula | | Amt (%) |
|---|---|---|
| ABF POOA | Glycerol Octanoate | 14.67% |
| | $H_2O_2$ 35% | 19.42% |
| | Water | 49.44% |
| | NaOH 50% | 16.47% |

TABLE 8B

| 5° C. Rxn | | 20° C. Rxn | | 30° C. Rxn | | 40° C. Rxn | |
|---|---|---|---|---|---|---|---|
| time | % POOA 5° C. | time | % POOA 20° C. | Time | % POOA 30° C. | time | % POOA 40° C. |
| 10 | 2.55 | 1 | 2.07 | 1 | | 1 | 5.19 |
| 20 | 3.45 | 5 | 3.89 | 3 | 4.56 | 3 | 6.23 |
| 30 | 3.90 | 10 | 4.77 | 5 | 5.24 | 5 | 6.06 |
| 40 | 4.20 | 15 | 5.46 | 10 | 6.35 | 7 | 5.36 |
| 50 | 4.20 | 20 | 5.83 | 15 | 6.57 | 10 | 5.40 |
| 60 | 4.50 | 25 | 6.30 | 20 | 6.52 | 15 | 3.38 |
| 70 | 4.72 | 30 | 6.67 | 30 | 6.29 | 20 | 3.82 |
| | | 40 | 6.77 | 45 | 5.60 | | |
| | | 50 | 6.73 | 90 | 4.36 | | |
| | | 70 | 6.61 | | | | |
| | | 90 | 6.36 | | | | |
| | | 160 | 5.66 | | | | |

Figure 3:
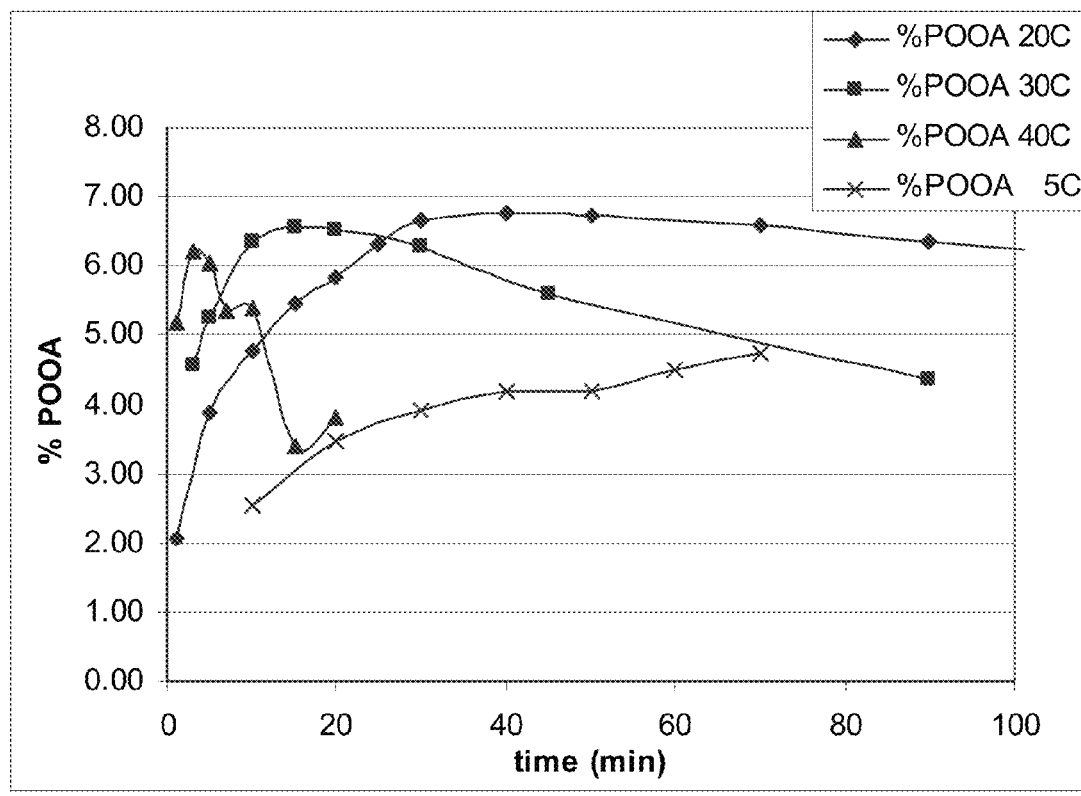
FIG. 3 shows a graph representing POOA concentration over time at various reaction temperatures according to various embodiments of the invention.

The results are shown in FIG. 3 (graphical representation of POOA concentration over time at various reaction temperatures). The graph confirms that under different environmental temperatures the concentration of available peracid is widely variable. The variability depends upon the temperature of the generator and temperature of the reactants (e.g. raw starting materials) and of the time point at which the reaction mixture would be used. These results demonstrate the importance of mechanisms for controlling the ex-situ peracid reaction temperature. The control of temperature impacts the kinetics of the reaction and therefore can be critical to consistency of peracid output according to the invention.

Example 7

Methods of thermal control were analyzed. The reaction rates of a single peracid chemistry (POOA) generated according to the invention were analyzed. The reagents set forth in Table 9A were used to generate POOA. The test utilized reactants that were stored at either 5° C. or 40° C. (as further shown in Table 9B) to represent the changes in (and ranges of) temperatures one skilled in the art may expect in practice.

TABLE 9A

| Reagent Formula | | Amt (%) |
|---|---|---|
| ABF POOA | Glycerol Octanoate | 9.83% |
| | $H_2O_2$ 35% | 13.02% |
| | Water (21.1° C.) | 65.90% |
| | NaOH 50% | 11.21% |

The test controlled the temperature of the reaction by controlling the vessel temperature where the reaction took place. The temperature was controlled to 20° C. (~69° F.). In this reaction the glycerol octanoate, peroxide and water reagents (e.g. raw starting materials) were added to the reaction vessel first. Once those ingredients were combined the 50% NaOH was added. For purposes of testing this reaction scheme was utilized as a result of the addition of NaOH both initiating the reaction and causing a large exothermic effect. Both temperature and resultant peracid were monitored in this reaction.

POOA production rates and temperature were monitored as a function of time with reaction vessel temperatures controlled to 20° C., wherein the reagents were stored at either 5° C. or 40° C. The results are shown in Table 9B.

TABLE 9B

| time (min) | temp with 5° C. reagents | temp with 40° C. reagents | POOA @ 5° C. | POOA @ 40° C. |
|---|---|---|---|---|
| 0 | 69 | 84 | 0 | 0 |
| 1 | 80 | 84 | 0.73 | 0.95 |
| 3 | 72 | 73 | 1.36 | 1.58 |
| 5 | 70 | 71 | 1.69 | 1.90 |
| 10 | 69 | 69 | 2.28 | 2.44 |
| 20 | 69 | 69 | 2.80 | 3.04 |
| 30 | 69 | 69 | 3.22 | 3.50 |
| 45 | 69 | 69 | 3.72 | 3.98 |
| 60 | 69 | 69 | 4.02 | 4.24 |
| 90 | 69 | 69 | 4.30 | 4.23 |
| 120 | 69 | 69 | 4.03 | 4.00 |
| 180 | 69 | 69 | | 3.57 |

Figure 4:
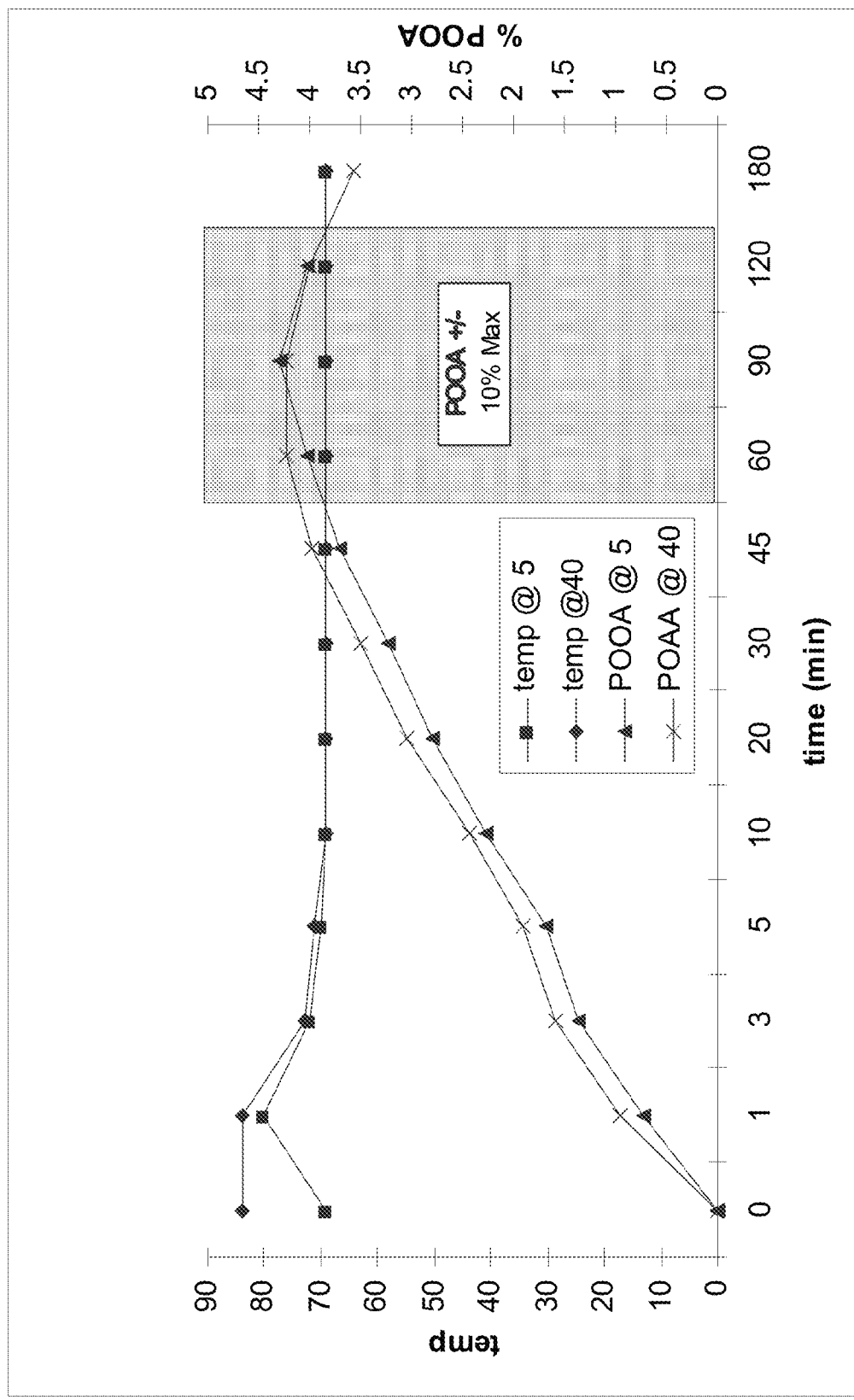
FIG. 4 shows a graph representing POOA production at various temperatures over a period of time according to various embodiments of the invention.

The results are further shown in the graph of FIG. 4. The identified time period from approximately 50 minutes to 120 minutes (shown in the boxed area of the graph) outlines where the 2 separate reaction mixtures (one with reagents starting at 5° C. and one with reagents starting at 40° C.) achieved maximum percentage POOA generation. These results demonstrate the ability to use temperature control as a means of driving toward consistency in the chemistry output 9 without regard to environmental temperatures under which the chemistry production takes place.

This example required increased time to achieve maximum generation of the peracid chemistry, notably about 50 minutes to achieve the +/−10% max target for peracid generation. However, as one skilled in the art of chemical reaction kinetics will ascertain, to decrease the time period for achieving maximum peracid generation the temperature of the reaction vessel and/or reaction manifold can be increased.

Example 8

Additional methods of thermal control were analyzed. The thermal control scheme outlined in Example 7 may add cost and/or complexity to an ABF system. As a result, improvements to the various methods for including temperature control were analyzed. An alternative was evaluated—heating one or more of the raw starting materials (i.e. reagents) for the ex-situ peracid composition. The heating of reagents as opposed to the reaction vessel where the chemical reaction is housed was evaluated as a means to control the reaction kinetics.

In this analysis water was selected as the raw starting material that was temperature controlled. Water was selected based on the fact that water tends to be the most abundant reagent in many peracid recipes according to the invention. In addition, the heating of water can be easily and inexpensively achieved as one skilled in the art will appreciate.

The reagents set forth in Table 10A were used to generate POOA.

TABLE 10A

| Reagent Formula | | Amt (%) |
|---|---|---|
| ABF POOA | Glycerol Octanoate | 9.83% |
| | $H_2O_2$ 35% | 13.02% |
| | Water | 65.90% |
| | NaOH 50% | 11.21% |

Table 10B shows the POOA production rates and temperature as a function of time with reagent temperatures controlled to variable temperatures −5° C. and 40° C., as opposed to temperature control of the reaction vessel and/or reaction manifold. The results are shown in Table 10B.

TABLE 10B

| time (min) | POOA 5° C. reagents | POOA 40° C. reagents | Rxn Temp 5° C. reagents | Rxn Temp 40° C. reagents |
|---|---|---|---|---|
| 0 | 0 | 0 | 89 | 94 |
| 1 | 1.26 | 1.65 | 109 | 117 |
| 3 | 2.30 | 2.68 | 106 | 112 |
| 5 | 2.82 | 3.16 | 103 | 108 |
| 10 | 3.56 | 3.65 | 96 | 100 |
| 15 | 3.70 | 3.87 | 85 | 94 |
| 20 | 3.83 | 3.83 | 87 | 89 |
| 30 | 3.92 | 3.76 | 80 | 81 |
| 45 | 3.90 | 3.63 | 74 | 75 |
| 60 | 3.80 | 3.52 | 72 | 72 |
| 90 | 3.62 | | 72 | |

Figure 5:
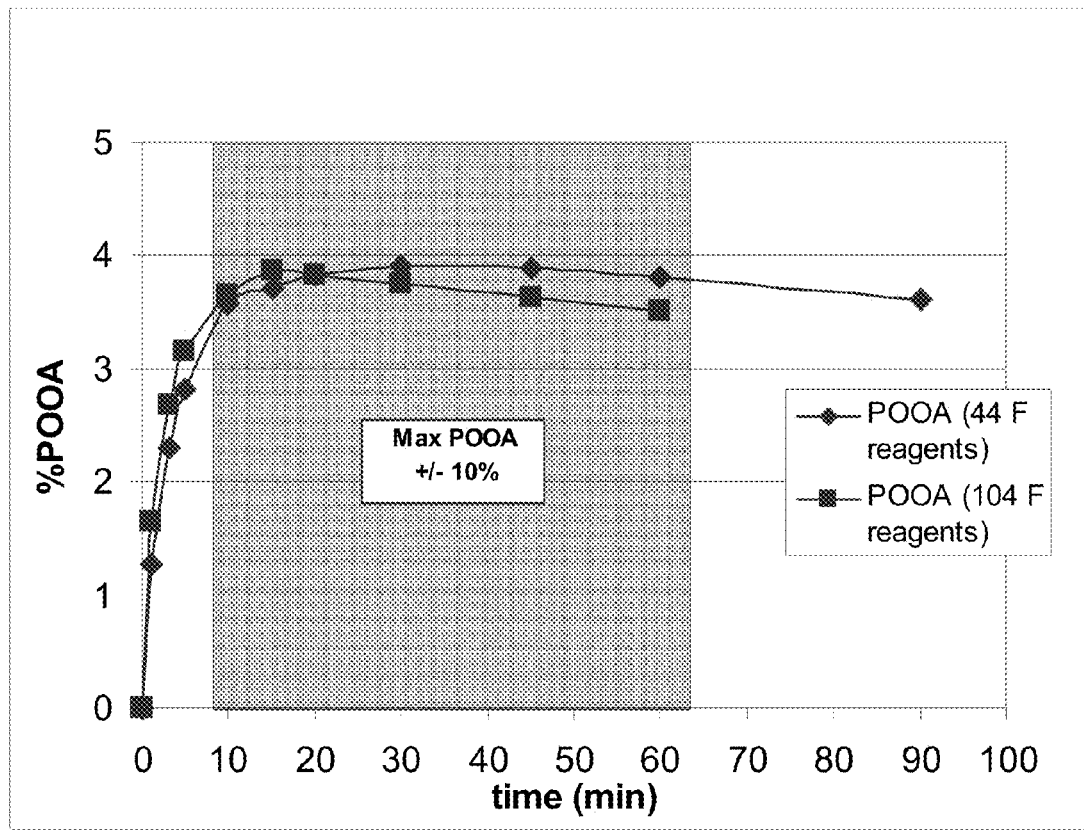
FIG. 5 shows a graph representing POOA production and temperature as a function of time according to various embodiments of the invention.

The results are further shown in the graph of FIG. 5. The results demonstrate the potential to use a heated water source to produce reaction kinetic rates with no other temperature controls of a system for generating the chemistry according to the invention.

Example 9

Concentrated premix formulations according to the invention were evaluated for peracid generation. The following premixes were utilized to generate the perhydrolysis compositions and final peracid concentrations set forth in Table 11.

perhydrolysis composition is then allowed to react for the time shown therein.

The resultant percentage of peracid generated in the chemistry is further shown demonstrating the utility of premix formulations for the generation of peracid chemistries according to the invention.

Example 10

The use of premix formulations for generating chemistry according to the invention was evaluated to determine the stability of various premix compositions as shown in Table 12. The use of a surfactant in premix formulation according to the invention includes a dispersant-effective amount for the meta-stability of the generated peracid solution (e.g. acidified), not the stability of the premix formulation. Accordingly, the use of a surfactant premix according to the invention, such as an ethanol-SLS premix (as outlined in Example 9) uses the surfactant (e.g. SLS) only for the physical stability of the perhydrolysis reaction mixture. In one tested embodiment, the amount of surfactant in the premix (less than about 2%) is significantly less than the levels needed to achieve a clear, transparent premix (at least about 9%). This result is from the ethanol solvent being the primary contributor of the premix stability. The surfactant-bleach activator interaction in the tested premix is in sufficient to generate a homogeneous premix.

Similarly, the use of a solvent premix, such as an ethanol premix, according to the invention does not include a dispersing agent.

TABLE 11

| Premix | Premix Components | Wt-% | Perhydrolysis Composition | Wt-% | Rxn Time (minutes) | Peracid % |
|---|---|---|---|---|---|---|
| SOA Premix | Glycerol Octanoate | 47.48 | SOA Premix | 27.60 | 5 | 3.93 |
| | H$_2$O$_2$ (50%) | 39.58 | NaOH (50%) | 13.45 | | |
| | Sulfonated Oleic Acid (SOA) (70%) | 12.95 | Water | 58.95 | | |
| NAS Premix | Glycerol Octanoate | 32.78 | NAS premix | 36.84 | 5 | 4.22 |
| | H2O2 (50%) | 30.36 | NaOH (50%) | 13.78 | | |
| | 1-Octanesulfonic acid, sodium salt (40%) | 14.52 | Water | 49.38 | | |
| | Water | 22.34 | | | | |
| Ethanol Premix | Glycerol Octanoate | 48.09 | Ethanol Premix | 27.60 | 5 | 5.20 |
| | H$_2$O$_2$ (50%) | 40.09 | NaOH (50%) | 13.45 | | |
| | Ethanol | 11.82 | Water | 58.95 | | |
| SLS-Ethanol Premix | Glycerol Octanoate | 46.40 | SLS-Ethanol premix | 24.85 | 8 | 4.03 |
| | H$_2$O$_2$ (50%) | 38.68 | NaOH (50%) | 12.12 | | |
| | SLS (30%) | 7.10 | Water | 63.03 | | |
| | Ethanol | 7.82 | | | | |
| SLS-Ethanol Premix 2 | Glycerol Octanoate | 47.17 | SLS-Ethanol premix | 27.31 | 8 | 5.41 |
| | H$_2$O$_2$ (50%) | 39.27 | NaOH (50%) | 13.32 | | |
| | SLS (30%) | 5.42 | Water | 59.37 | | |
| | Ethanol | 8.13 | | | | |
| SLS-H$_2$O$_2$ Premix | H$_2$O$_2$ (35%) | 91.19 | Glycerol Octanoate | 12.88 | 8 | 5.17 |
| | SLS (30%) | 8.81 | SLS-H2O2 premix | 16.80 | | |
| | | | NaOH (50%) | 13.32 | | |
| | | | Water | 57.00 | | |

The results of Table 11 show the various examples of concentrated premix formulations suitable for use according to the invention. The premix is provided in a concentrated formulation and then added to the remaining perhydrolysis composition as shown in the table. The premix formulation is diluted with the remaining reagents of the perhydrolysis composition, which is often referred to as a tank dilution. The

TABLE 12

| Premix | Premix Components | Wt % | Physical Appearance |
|---|---|---|---|
| Ethanol Premix | Glycerol Octanoate | 48.09 | Clear one phase |
| | H2O2 (50%) | 40.09 | |
| | Ethanol | 11.82 | |

TABLE 12-continued

| Premix | Premix Components | Wt % | Physical Appearance |
|---|---|---|---|
| SLS—Ethanol Premix | Glycerol Octanoate | 47.17 | Clear one phase |
| | H2O2 (50%) | 39.27 | |
| | Ethanol | 8.13 | |
| | SLS (30%) | 5.42 | |
| SLS—Premix | Glycerol Octanoate | 47.17 | Two phases |
| | H2O2 (50%) | 39.27 | |
| | Water | 8.13 | |
| | SLS (30%) | 5.42 | |

Example 11

Perhydrolysis studies at varying pH ranges were evaluated. In particular, the perhydrolysis rates of the ester source Monocaprin-100 (Abitec), a glycerol monooctanoate as a function of pH were evaluated. The reagents set forth in Table 13A were used to generate POOA according to the pH and formulations reacted to different stop times set forth in Table 13B. Table 13C shows the percentage of peracid generated after acidification at varying reaction stop times at the different pH.

TABLE 13A

| | Amt (%) |
|---|---|
| Monocaprin-100 | 10.1 |
| $H_2O_2$ 35% | 13.37% |
| Water | 18.94% |
| NaOH 10% | 57.6% |

TABLE 13B

| pH | NaOH used, g | Makeup DI-H2O, g | start time, min | stop times, min | | |
|---|---|---|---|---|---|---|
| | | | | 10 min | 20 min | 30 min |
| 12.45 | 57.6 | 0.00 | 0 | 10 | 20 | 30 |
| 11.45 | 34.6 | 23.00 | 2 | 12 | 22 | 32 |
| 11.04 | 26.6 | 31.00 | 4 | 14 | 24 | 34 |

TABLE 13C

| Sample | pH | Perhydrolysis Time: (% POOA post quench) (minutes of reaction) | | | MG % | MG pot POOA % | DG % | DG pot POOA % | Tot. Pot. POOA % | Yield of Pot. % |
|---|---|---|---|---|---|---|---|---|---|---|
| | | 10 | 20 | 30 | | | | | | |
| #1 | 12.45 | 2.20% | 2.84% | 2.89% | 38.20% | 2.83 | 15.60% | 1.47 | 4.30 | 67% |
| #2 | 11.45 | 1.32% | 1.45% | 1.52% | 38.20% | 2.83 | 15.60% | 1.47 | 4.30 | 35% |
| #3 | 11.04 | 0.88% | 0.84% | 0.71% | 38.20% | 2.83 | 15.60% | 1.47 | 4.30 | 17% |

Figure 6:
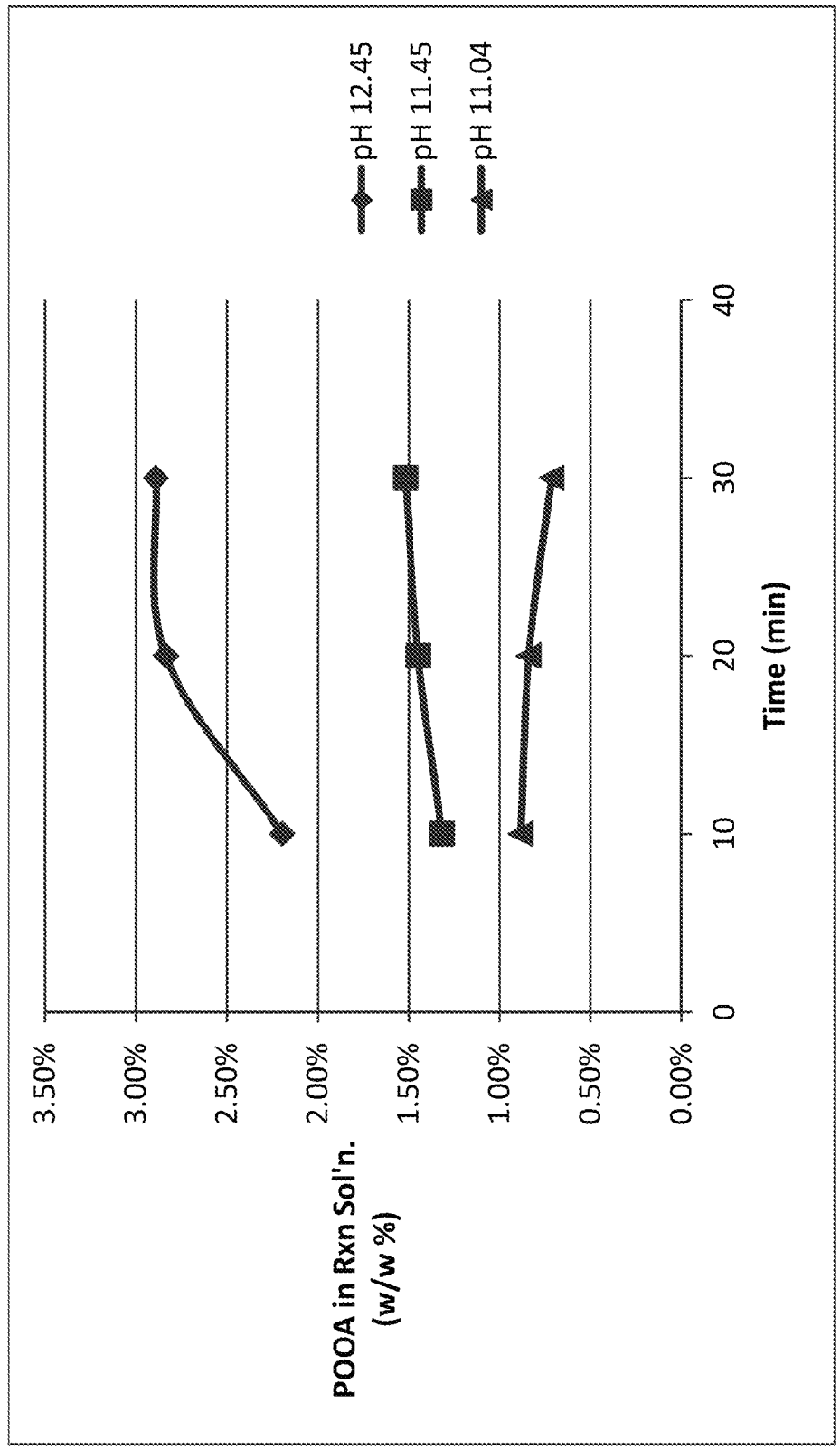
FIG. 6 shows a graph of peracid generated in a reaction solution according to the invention at varying pH.

The results are shown in FIG. 6 wherein the varying amounts of peracid (POOA) generated are compared to the reacted pH. The results indicate the benefit of undergoing the perhydrolysis reaction to generate peracid at a pH above 12, preferably above about 12.5. While it is not surprising that perhydrolysis processes are sped up at higher pHs, it is surprising that the degradation rate is significantly slower from pH 11.04 to pH 12.45.

Example 12

A variety of surfactants were analyzed for coupling and/or dispersion stabilizing of a peroxycarboxylic acid composition generated according to the methods of the invention. In particular, a peroxyoctanoic acid (POOA) composition in deionized water produced according to the invention was analyzed for coupling and/or dispersion stabilization using the dispersing agents set forth in Table 14A.

Given the very limited water solubility of POOA in its protonated form, acidification of the alkaline perhydrolysis solutions of the same causes immediate precipitation and rapid phase separation. In this example various surfactants and hydrotropes were evaluated for their ability to couple the POOA. In Table 14A it can be seen that the most efficient agents for coupling an already precipitated solution of POOA were samples I and II. SLS and LAS showed the greatest efficacy in coupling and dispersion of the POOA solutions, requiring 0.64 g/200 g aqueous POOA.

TABLE 14A

| Sample | (A) Concentration of POOA (ppm) in DI Water | (B) Surfactant-Dispersant | Amount of (B) Required for Coupling (g/200 g aq POOA) |
|---|---|---|---|
| I | 1000 | Sodium Lauryl Sulfate (SLS) | 0.64 |
| II | 1000 | Linear Aryl Sulfonate (LAS) | 0.65 |
| III | 1000 | Sodium Lauryl Ether Sulfate (SLES) | >0.94 |
| IV | 1000 | Pluronic 25R2 (AE) | >>0.74 |
| V | 1000 | Amine oxide (AO) | >3.58 |
| VI | 1000 | Alkyl Polyglycosides (APG) | 2.46 |
| VII | 1000 | Sodium octanesulfonate (NAS-FAL) | 6.60 |
| VIII | 1000 | Sorbitan monolaurate ethoxylate (Tween 20) | >2.59 |
| IX | 1000 | Alcohol ethoxylate (Pluronic L24-5) | >2.0 |
| X | 1000 | Sodium dioctyl Sulfosuccinates (NaDOSS) | >2.0 |

The SLS, LAS and SOA dispersing agents were then further examined for efficacy in stabilizing and/or dispersing in 1% or lower sulfuric acid solutions. Solutions were made according to the following order (3, 6, 9, 12, 1, 4, 7, 10, 2, 5, 8, 11, 13, 14). Solution 13 was made as 1 through 12 with the addition of 50 mL of 5 grain hard water to the aliquot of alkaline reaction solution followed by swirling with the surface aliquot and then additional 50 mL of 5 grain hard water, followed within about 5 seconds by 50 mL of 5 grain 2% sulfuric acid and swirled. Solution 14 was made by direct addition of 1% sulfuric acid (5 grain) without pre-dilution, but after moments of swirling with SLS aliquot. All concentrations are shown in ppm.

For the POOA solutions the targeted peracid concentration was based upon initial average of about 5.40 wt-% of ongoing cold alkaline peracid hydrolysis according to the invention (**), wherein the aliquot was constant while POOA was increasing.

While coupling in this case is defined as clarifying or reducing the opacity of an otherwise cloudy POOA solution, the same surfactants were found to be very efficient at stabilizing acidic, aqueous dispersions of POOA as shown in Table 14B. The appearance of an oil sheen was regarded as a pass or fail. From this data it can be seen that SLS is an exceptional dispersant for acidified POOA.

TABLE 14B

| | **POOA | $H_2SO_4$ | LAS | SOA | SLS | oil sheen at 1 h | oil sheen at 23 h | Bulk POOA at 15 min | Bulk POOA at 1 h | Bulk POOA at 23 h | Rxn sol'n POOA |
|---|---|---|---|---|---|---|---|---|---|---|---|
| 1 | 1,000 | 10,000 | 100 | | | dense cloudy | no | yes | | | | 5.78% to 5.92% |
| 2 | 1,000 | 10,000 | | 100 | | dense cloudy | no | yes | | | | 5.92% to 6.11% |
| 3 | 1,000 | 10,000 | | | 100 | light cloudy | no | no | 1054 | 981 | 638 | 5.40% to 5.78% |
| 4 | 1,000 | 10,000 | 200 | | | dense cloudy | no | yes | | | | 5.78% to 5.92% |
| 5 | 1,000 | 10,000 | | 200 | | dense cloudy | no | yes | | | | 5.92% to 6.11% |
| 6 | 1,000 | 10,000 | | | 200 | almost clear | no | no | 1055 | 1016 | 523 | 5.40% to 5.78% |
| 7 (control) | 750 | 10,000 | 100 | | | dense cloudy | no | * yes | | | | 5.78% to 5.92% |
| 8 | 750 | 10,000 | | 100 | | dense cloudy | no | yes | | | | 5.92% to 6.11% |
| 9 | 750 | 10,000 | | | 100 | light cloudy | no | no | 773 | 748 | 408 | 5.40% to 5.78% |
| 10 | 750 | 10,000 | 200 | | | dense cloudy | no | yes | | | | 5.78% to 5.92% |
| 11 | 750 | 10,000 | | 200 | | dense cloudy | no | yes | | | | 5.92% to 6.11% |
| 12 | 750 | 10,000 | | | 200 | almost clear | no | no | 802 | 734 | 323 | 5.40% to 5.78% |
| ***13 | 1,000 | 10,000 | none | none | none | Initially cloudy | yes | yes | | | | 5.40% |
| ****14 | 750 | 10,000 | | | 100 | semi dense cloudy | no | no | | | | |

Table 14B shows that the only non-SLS dispersing agent that approaches the passing of stability of the POOA solution at 23 hours is LAS, demonstrating minimal surface oil (*). The inventions being thus described, it will be obvious that the same may be varied in many ways. Such variations are not to be regarded as a departure from the spirit and scope of the inventions and all such modifications are intended to be included within the scope of the following claims.

What is claimed is:

1. A peroxycarboxylic acid forming composition comprising:

a first reagent premix comprising at least one ester of a polyhydric alcohol and a C5 to C18 carboxylic acid with HLB value of 3 or greater, an organic solvent selected from the group consisting of methanol, ethanol, propanol, isopropanol, butanol, an ether, a ketone, and combinations thereof, wherein said organic solvent solubilizes the ester; a dispersing agent, wherein the dispersing agent is a sulfonated oleic acid, 1-octanesulfonic acid, or sodium lauryl sulfonates; and one or more agents selected from the group consisting of an oxidizing agent, water, and mixtures thereof; wherein the dispersing agent is sufficient to create a physically meta-stable solution upon reaction with a source of alkalinity; and a second reagent source comprising the source of alkalinity; wherein said composition is not at equilibrium, and has a pH greater than 12.

2. The composition of claim 1, wherein the carboxylic acid comprises a C5 to C18 carboxylic acid and wherein the polyhydric alcohol is selected from the group consisting of a sugar, a sugar alcohol, and mixtures and derivatives thereof.

3. The composition of claim 1, wherein the polyhydric alcohol is selected from the group consisting of ethylene glycol, propylene glycol, glycerol, sorbitol, sorbitan, and mixtures and derivatives thereof and wherein the ester is selected from the group consisting of glycerol monooctanoate, glycerol dioctanoate, glycerol trioctanoate, sorbitan monooctanoate, sorbitan dioctanoate, sorbitan trioctanoate, laurate sucroside and mixtures and derivatives thereof and wherein the oxidizing agent comprises a hydrogen peroxide donor.

4. The composition of claim 1, wherein the oxidizing agent comprises hydrogen peroxide or a source of hydrogen peroxide selected from the group consisting of a percarbonate, a perborate, urea hydrogen peroxide, PVP-peroxides and mixtures thereof.

5. The composition of claim 1, wherein the source of alkalinity is selected from the group consisting of an alkaline metal hydroxide, an alkaline earth metal hydroxide, an alkali metal silicate, an alkali metal carbonate, borates and mixtures thereof.

6. The composition of claim 1, wherein the reagent premix consists of at least one ester of a polyhydric alcohol and a C5 to C18 carboxylic acid with HLB value of 3 or greater, an oxidizing agent, a dispersing agent, and a solvent.

7. The composition of claim 6, wherein the reagent premix consists of at least one ester of a polyhydric alcohol and a C5 to C18 carboxylic acid with HLB value of 3 or greater, an oxidizing agent, and a dispersing agent.

8. A peroxycarboxylic acid forming composition comprising:
a first reagent premix comprising at least one ester of a polyhydric alcohol and a C5 to C18 carboxylic acid with HLB value of 3 or greater, an organic solvent selected from the group consisting of methanol, ethanol, propanol, isopropanol, butanol, an ether, a ketone, and combinations thereof, an oxidizing agent and a dispersing agent; wherein the dispersing agent is a sulfonated oleic acid, 1-octanesulfonic acid, or sodium lauryl sulfonates and in an amount sufficient to create a physically metastable solution upon reaction with a source of alkalinity; wherein said organic solvent solubilizes the ester; and
a second reagent source comprising a source of alkalinity; wherein said composition is not at equilibrium, and has a pH greater than 12.

9. The composition of claim 8, wherein the first reagent premix comprises an ester of a C5 to C11 carboxylic acid, and further comprises a C1 to C4 carboxylic acid ester, wherein at least one ester has an HLB value of 3 or greater, and wherein the esters are selected from the group consisting of glycerol monooctanoate, glycerol dioctanoate, glycerol trioctanoate, sorbitan monooctanoate, sorbitan dioctanoate, sorbitan trioctanoate, laurate sucroside and mixtures and derivatives thereof.

10. The composition of claim 9, wherein the reagent premix further comprises water.

11. The composition of claim 8, wherein the oxidizing agent comprises hydrogen peroxide or a hydrogen peroxide source selected from the group consisting of a percarbonate, a perborate, urea hydrogen peroxide, PVP-peroxides and mixtures thereof.

12. The composition of claim 8, wherein the source of alkalinity is selected from the group consisting of an alkaline metal hydroxide, an alkaline earth metal hydroxide, an alkali metal silicate, an alkali metal carbonate and mixtures thereof.

13. The composition of claim 8, wherein the reagent premix comprises glycerol octanoate and hydrogen peroxide.

14. The composition of claim 13, wherein the reagent premix comprises glycerol octanoate, hydrogen peroxide, sodium lauryl sulfonate and an alcohol solvent.

15. A method for delivering an antimicrobial a surface comprising providing a single or mixed peroxycarboxylic acid antimicrobial composition formed by diluting a composition first reagent premix comprising at least one ester of a polyhydric alcohol and a C5 to C18 carboxylic acid with HLB value of 3 or greater, an organic solvent selected from the group consisting of methanol, ethanol, propanol, isopropanol, butanol, an ether, a ketone, and combinations thereof, an oxidizing agent, and a dispersing agent, and a second reagent source comprising a source of alkalinity, with an aqueous acidic solution to a pH of about 1 to about 8, wherein the solvent is an organic solvent to solubilize the ester; and wherein the dispersing agent is a sulfonated oleic acid, 1-octanesulfonic acid, or sodium lauryl sulfonates and in an amount sufficient to create a physically meta-stable solution upon reaction with a source of alkalinity.

16. A method for forming an antimicrobial composition, said method comprising:
(a) providing a peroxycarboxylic acid composition having active peroxycarboxylic acid content from about 0.25% to about 20% comprising:
(i) a first reagent premix comprising at least one ester of a polyhydric alcohol and a C5 to C18 carboxylic acid with HLB value of 3 or greater, an organic solvent selected from the group consisting of methanol, ethanol, propanol, isopropanol, butanol, an ether, a ketone, and combinations thereof, a dispersing agent, and one or more agents selected from the group consisting of an oxidizing agent, water, and mixtures thereof; wherein the solvent solubilizes the ester; wherein the dispersing agent is a sulfonated oleic acid, 1-octanesulfonic acid, or sodium lauryl sulfonates and in an amount sufficient to create a physically meta-stable solution upon reaction with a source of alkalinity; and
(ii) a second reagent source comprising a source of alkalinity; wherein said composition has a pH greater than 12 and is not at equilibrium;
(b) diluting the generated peroxycarboxylic acid composition to an active peroxycarboxylic acid content from about 0.01% to about 1%;
(c) providing an acidic aqueous solution; and
(d) diluting the peroxycarboxylic acid composition with the acidic aqueous solution to a pH of about 1.0 to about 8.0 to form the antimicrobial composition.

17. The method of claim 16, wherein the peroxycarboxylic acid composition is allowed to react for a sufficient amount of time such that a C5 to C18 percarboxylic acid is formed.

18. The method of claim 17, wherein the peroxycarboxylic acid composition has a pH greater than about 12.5 and wherein the dilution of the peroxycarboxylic acid composition generates an active peroxycarboxylic acid content of about 0.01% to about 0.1%.

19. The method of claim 18, wherein the antimicrobial composition having a pH of about 1.0 to about 8.0 is further diluted to a use solution having an active peroxycarboxylic acid content of about 1 ppm to about 100 ppm.

20. A method for forming an antimicrobial composition, said method comprising:
(a) providing a peroxycarboxylic acid composition having active peroxycarboxylic acid content from about 0.25% to about 20% comprising:
(i) a first reagent premix comprising at least one ester of a polyhydric alcohol and a C5 to C18 carboxylic acid with HLB value of 3 or greater, an organic solvent selected from the group consisting of methanol, ethanol, propanol, isopropanol, butanol, an ether, a ketone, and combinations thereof, a dispersing agent, and one or more agents selected from the group consisting of an oxidizing agent, water, and mixtures thereof; wherein the dispersing agent is a sulfonated oleic acid, 1-octanesulfonic acid, or sodium lauryl sulfonates and in an amount sufficient to create a physically meta-stable solution upon reaction with a source of alkalinity; and (ii) a second reagent source comprising a source of alkalinity; wherein said composition has a pH greater than 12 and is not at equilibrium;

(b) allowing the peroxycarboxylic acid composition to react for a sufficient amount of time such that a C5 to C18 percarboxylic acid is formed to generate a antimicrobial composition; and (c) providing antimicrobial composition to an application for use without an acidification step.

21. The method of claim 20, wherein the antimicrobial composition is further diluted within a use application.

22. The method of claim 20, wherein the antimicrobial composition is substantially free of a stabilizing agent.

* * * * *